(12) United States Patent
Iwakiri et al.

(10) Patent No.: US 8,861,680 B2
(45) Date of Patent: Oct. 14, 2014

(54) RADIOLOGICAL IMAGE DETECTION APPARATUS AND RADIOGRAPHIC IMAGING CASSETTE

(75) Inventors: Naoto Iwakiri, Kanagawa (JP); Haruyasu Nakatsugawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 331 days.

(21) Appl. No.: 13/361,743

(22) Filed: Jan. 30, 2012

(65) Prior Publication Data

US 2012/0219114 A1 Aug. 30, 2012

(30) Foreign Application Priority Data

Feb. 24, 2011 (JP) ................. 2011-038953

(51) Int. Cl.
  *H05G 1/64* (2006.01)
  *G03B 42/04* (2006.01)
  *A61B 6/00* (2006.01)
(52) U.S. Cl.
  CPC ............... *G03B 42/04* (2013.01); *A61B 6/4283* (2013.01); *A61B 6/4233* (2013.01)
  USPC .......................................... 378/98.8; 378/189
(58) Field of Classification Search
  USPC ................. 378/98.8, 189; 250/370.09, 370.11
  See application file for complete search history.

(56) References Cited

U.S. PATENT DOCUMENTS

| | | | |
|---|---|---|---|
| 8,642,967 B2 * | 2/2014 | Iwakiri et al. ............. | 250/361 R |
| 2002/0014592 A1 * | 2/2002 | Rutten et al. ............. | 250/370.11 |
| 2002/0014594 A1 | 2/2002 | Endo | |
| 2006/0038132 A1 | 2/2006 | Hayashida | |
| 2006/0065863 A1 * | 3/2006 | Takasu et al. .................. | 250/581 |
| 2008/0251729 A1 * | 10/2008 | Saito et al. ............... | 250/370.09 |
| 2010/0193691 A1 | 8/2010 | Ishii et al. | |
| 2010/0243908 A1 | 9/2010 | Shoji et al. | |
| 2011/0006213 A1 * | 1/2011 | Sato et al. ...................... | 250/367 |

FOREIGN PATENT DOCUMENTS

| | | | |
|---|---|---|---|
| JP | 2002-014168 A | | 1/2002 |
| JP | 2006-058124 A | | 3/2006 |
| JP | 2008-235649 A | | 10/2008 |
| JP | 2009-133837 A | | 6/2009 |
| JP | 2010075605 A | * | 4/2010 |
| JP | 2011-017683 A | | 1/2011 |
| WO | 2009/031574 A1 | | 3/2009 |

OTHER PUBLICATIONS

An Office Action; "Notice of Reason for Rejection," issued by the Japanese Patent Office on Jan. 7, 2014, which corresponds to Japanese Patent Application No. 2011-038953 and is related to U.S. Appl. No. 13/361,743; with English language translation.

* cited by examiner

*Primary Examiner* — Glen Kao
(74) *Attorney, Agent, or Firm* — Studebaker & Brackett PC

(57) ABSTRACT

A radiological image detection apparatus includes: a radiological image detection apparatus main body including a scintillator that converts into fluorescence radiation emitted by way of a subject and a photodetecting unit provided on a radiation entrance side of the scintillator; and a support disposed on a radiation entrance side of the radiological image detection apparatus main body to support the subject, in which the photodetecting unit includes a thin film portion that detects the fluorescence as an electric signal and a reinforcing member that is provided on another side of the thin film portion with respect to its side facing the scintillator; and the reinforcing member and the support are bonded together and remain in close contact with each other along a joint plane therebetween.

19 Claims, 18 Drawing Sheets

RADIOLOGICAL IMAGE DETECTION APPARATUS AND RADIOGRAPHIC IMAGING CASSETTE

CROSS-REFERENCE TO RELATED APPLICATIONS

This application is based on and claims priority under 35 USC 119 from Japanese Patent Application No. 2011-038953 filed on Feb. 24, 2011; the entire content of which is incorporated herein by reference.

BACKGROUND

1. Technical Field

The present invention relates to a radiological image detection apparatus and a radiographic imaging cassette used in a X-ray imaging system, or the like.

2. Related Art

DR (Digital Radiography) using a radiological image detection apparatus, like an FPD (Flat Panel Detector) that converts a radiological image, such as an X-ray image, into digital data, has recently been put into practice. When compared with a related art CR (Computed Radiography) system that uses an imaging plate made of a photostimulable phosphor (an accumulative phosphor), the radiological image detection apparatus has an advantage of being able to ascertain an image immediately. Thus, the DR has become proliferated rapidly.

Various types of radiological image detection apparatuses have already been put forward. One of the radiological image detection apparatuses is of a known indirect conversion type. This type of radiological image detection apparatus temporarily converts X-radiation into visible light by means of a scintillator, like a CsI:Tl scintillator and a GOS ($Gd_2O_2S$:Tb) scintillator, and a semiconductor layer converts the visible light into electric charges and accumulates the resultant electric charges (see; for instance, Patent Document 1 (JP-A-2011-17683)).

In the X-ray image detection apparatus described in connection with Patent Document 1, X radiation is emitted from a photodetecting unit to the scintillator. Specifically, the photodetecting unit is disposed on a side of the scintillator facing a subject (a patient), and a light detector is disposed opposite a back side of a support member that supports the subject. Also, as described in Patent Document 1, a panel made up of the light detector and the scintillator can be affixed directly to the support member. However, where the support member and the panel are affixed together, attention must be paid in such a way that the support member can easily be replaced.

Moreover, where a main body of the X-ray image detection apparatus is accommodated in a housing, to thus be formed as a cassette, the light detector opposes a back side of a ceiling of the housing. The cassette is made slim by means of affixing the thus-positioned light detector directly to the ceiling.

In a configuration where the light detector is placed on an X radiation entrance side (i.e., a subject side) of the scintillator like that mentioned above, a short distance lies between a principal light emission area on the X radiation entrance side and the photodetecting unit of the scintillator, a high definition detected image is acquired. In the meantime, a substrate of the photodetecting unit placed on the X radiation entrance side of the scintillator unavoidably absorbs X radiation. Therefore, there is a drawback of the amount of X radiation incident on the scintillator being reduced as a result of X radiation being absorbed by the substrate.

The photodetecting unit is built by inclusion of a photodiode (PD) and a TFT (Thin Film Transistor) that each are formed from a-Si, or the like. Alkali-free glass is usually used for a substrate supporting the PD and the TFT. The reason for this is that, when soda glass is used, a-Si may be contaminated with Na that will stem from glass during formation of an a-Si film in the presence of high temperature, which may in turn deteriorate performance of an element. However, alkali-free glass is more expensive than soda glass and also absorbs a larger amount of X radiation than does the soda glass. For instance, when an X-ray shaped beam generated at a tube voltage of 50 kV is used by applying a filter having 2 mm aluminum equivalent to the photodetecting unit, an X-ray absorption factor exhibited by the alkali-free glass substrate comes to as high as 16.8%. Specifically, the light reaches the scintillator while 15% or more of X radiation with which the photodetecting unit has been irradiated is lost as a result of X radiation being absorbed by the substrate. As mentioned above, when consideration is given to maintaining the performance of the a-Si film, using alkali-free glass for the substrate is indispensable. As a result of X radiation being absorbed by the substrate, a great decline in the amount of X radiation entering the scintillator is unavoidable. Specifically, a high image quality feature that is yielded when the scintillator is exposed to X radiation emitted from the direction of the photodetecting unit is diminished.

Incidentally, if the radiological image detection apparatus not having a substrate in the photodetecting unit can be built, the radiological image detection apparatus will be preferable that absorption of radiation, which would otherwise be caused by the substrate, can be avoided. In Patent Document 2 (JP-A-2009-133837) and Patent Document 3 (JP-A-2008-235649), after a thin film portion, such as a PD and a TFT, has been formed on a substrate, the substrate is peeled off and eliminated. In this case, a panel that is a laminate made up of a scintillator and the thin film portion will become easily deflected under the weight of the scintillator. If the panel remains deflected, clearance will arise between a support member and the panel. When experienced impact, the panel will become rattle, which in turn may inflict damage on the scintillator. In order to prevent deflection of the panel, the support member that supports a subject and the thin film portion must be firmly bonded together substantially in their entirety.

As mentioned above, in order to enhance, to a much greater extent, image quality of the X-ray image detection apparatus of the type in which radiation is emitted from the direction of the photodetecting unit of the scintillator, a radiological image detection apparatus including a substrate-free photodetecting unit is desired. However, if the substrate is separated as described in Patent Documents 2 and 3, the scintillator, the thin film portion, and the support member must be firmly bonded in their entirety in order to prevent occurrence of deflection. If they are firmly bonded in their entirety, replacement of the support member will become difficult. Further, when the support member and the panel are separated from each other, the thin film portion will be damaged. CFRP (Carbon Fiber Reinforced Plastic); for instance, is used for the support member. When a surface of the support member is flawed, fibers are broken, to thus become finely split. The thus-split support member may give discomfort to the patient or be liable to become unsanitary. Flaws in the support member also lead to occurrence of a defect in a detected image. When compared with the support member, the panel is expensive. Discarding the panel every time the support member is replaced is uneconomical. For this reason, replacement of the support member is indispensable. Specifically, easily-separable bonding of the panel to the support member is important.

SUMMARY

An illustrative aspect of the invention is to provide a radiological image detection apparatus and a radiographic imaging cassette that enable enhancement of impact resistance and ease of rework of a support member, such as replacement, by solving the drawbacks which will arise when a photodetecting unit does not have any substrate and that also enable further improvement in image quality.

According to an aspect of the invention, a radiological image detection apparatus includes: a radiological image detection apparatus main body including a scintillator that converts into fluorescence radiation emitted by way of a subject and a photodetecting unit provided on a radiation entrance side of the scintillator; and a support disposed on a radiation entrance side of the radiological image detection apparatus main body to support the subject. The photodetecting unit includes a thin film portion that detects the fluorescence as an electric signal and a reinforcing member that is provided on another side of the thin film portion with respect to its side facing the scintillator. The reinforcing member and the support are bonded together and remain in close contact with each other along a joint plane therebetween.

According to another aspect of the invention, a radiographic imaging cassette includes the aforementioned radiological image detection apparatus. The radiological image detection apparatus main body is accommodated in a housing formed by inclusion of the support.

According to another aspect of the invention, a radiographic imaging system includes: a radiation source that emits radiation to a subject; a support; and the aforementioned radiological image detection apparatus.

According to another aspect of the invention, a radiological image detection apparatus includes: a scintillator that converts radiation emitted by way of a subject into fluorescence and a photodetecting unit provided on a radiation entrance side of the scintillator. The photodetecting unit has a thin film portion for detecting the fluorescence as an electric signal and a reinforcing member disposed on another side of the thin film portion with respect to its side facing the scintillator. The reinforcing member and a support for supporting the subject are bonded together and remain in close contact with each other along a joint plane therebetween.

With the configurations discussed above, even when a substrate is peeled off from a thin film portion of a photodetecting unit, the thin film portion is supported by a reinforcing member, to thus be reinforced. As a result of such a reinforcing member being provided, a scintillator and the thin film portion do not undergo inadvertent deflection. The scintillator, the thin film portion, a laminate (panel) of the reinforcing member, and a support member are integrated along a joint plane while held in close contact with each other. It is thereby possible to prevent occurrence of clearance among opposite surfaces of the scintillator, the thin film portion, and the support member. Infliction of damage to the scintillator, or the like, which would otherwise arise when the scintillator undergoes impact as a result of colliding against the support, can be prevented, whereby impact resistance of the radiological image detection apparatus can be enhanced. According to the present invention, since the reinforcing member is interposed between the support member and the thin film portion, the panel and the support member can be readily separated from each other without impairing the thin film portion. Further, when the panel including the reinforcing member and the support member are brought into close contact with each other along the joint plane, it is possible to obviate a necessity for firmly bonding the panel to the support member in their entirety, so that separation of the panel from the support member can be facilitated further. Ease of rework of the radiological image detection apparatus can thereby be enhanced.

As mentioned above, a problem, which would arise when the substrate of the photodetecting unit is separated, is resolved. Hence, an effect of an improvement in image quality which is yielded when the scintillator is exposed to X radiation emitted from the direction of the photodetecting unit can be sufficiently accomplished.

DETAILED DESCRIPTION

Figure 1:
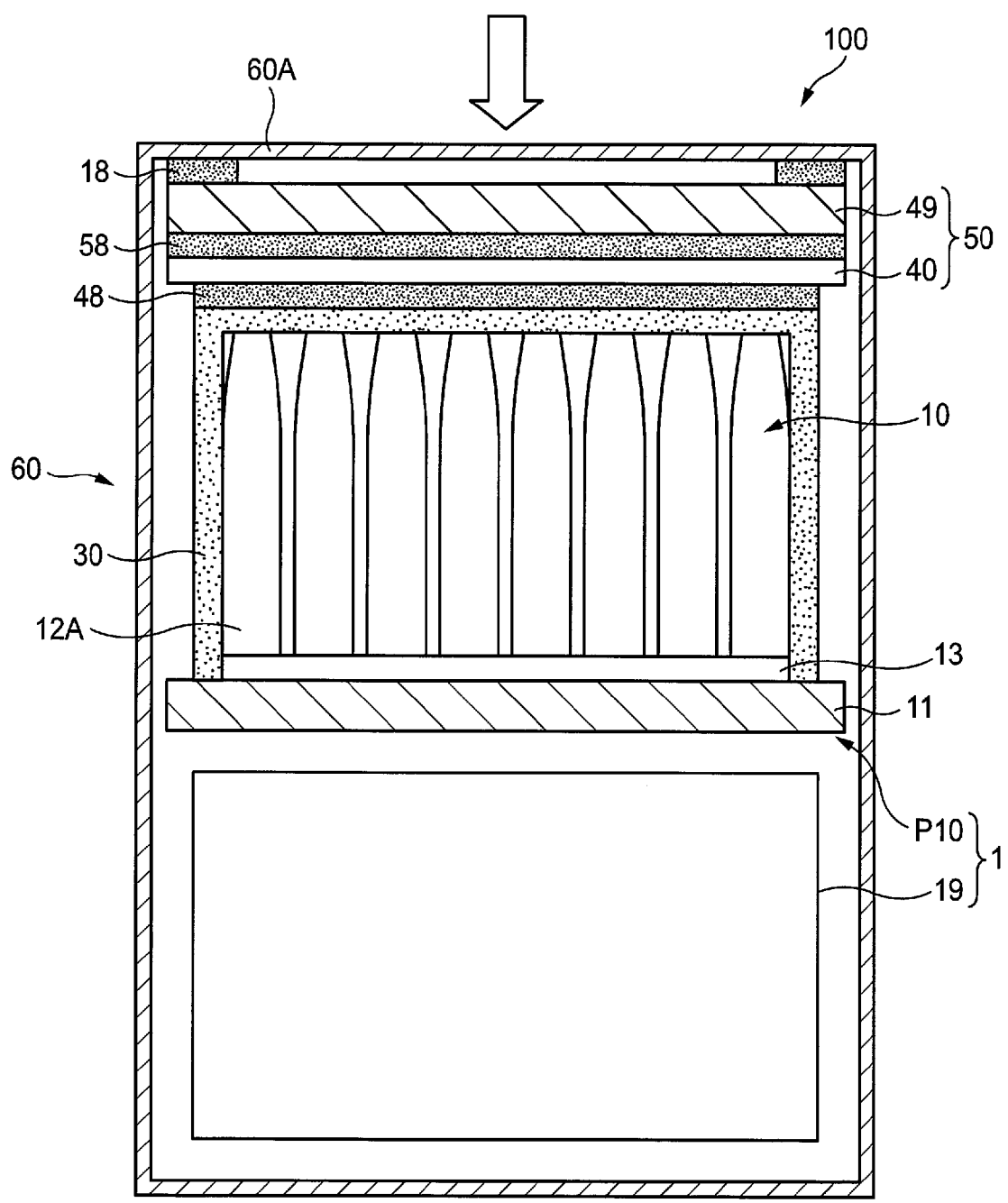
FIG. 1 is a side cross sectional view schematically showing a general configuration of an X-ray imaging cassette.

An example X-ray image detection apparatus (a radiological image detection apparatus) for explaining an embodiment of the present invention is hereunder described by reference to FIGS. 1 through 11.

A configuration analogous to the previously-described configuration is assigned the same reference numerals, and its repeated explanations are omitted or simplified for brevity.

1. Overall Configuration

FIG. 1 is a side cross sectional view schematically showing a general configuration of an X-ray imaging cassette 100 of indirect conversion type. The X-ray imaging cassette 100 has a main body 1 serving as a radiological image detection apparatus main body and a housing 60 for accommodating the main body 1.

The main body 1 is equipped with a scintillator 10 that includes a fluorescent material which emits fluorescence upon exposure to X radiation (indicated by an outlined arrow shown in FIG. 1); a photodetecting unit 50 that is disposed on an X-ray entrance side of the scintillator 10 and that detects the fluorescence emitted from the scintillator 10 as an electric signal; and a control module 19 that is disposed opposite the X-ray entrance side of the scintillator 10.

The control module 19 includes a circuit board on which there are implemented an IC serving as a control block for activating and controlling the photodetecting unit 50, an IC for processing an image signal, and the like, and a power circuit. The control module 19 is assembled into the scintillator 10 and the photodetecting unit 50.

The housing 60 accommodates the scintillator 10, the photodetecting unit 50, and the control module 19. An actual thickness of the scintillator 10 and an actual thickness of the photodetecting unit 50 are different from and smaller than those shown in FIG. 1 that is a schematic diagram. Therefore, the housing 60 is also made thinner than that shown in FIG. 1. The scintillator 10 and the photodetecting unit 50 are layered in an integrated manner in the form of a panel. In subsequent descriptions, a laminate including the scintillator 10 and the photodetecting unit 50 is sometimes called an X-ray image detection panel P10.

The housing 60 has a top plate 60A located on an X-ray entrance side of the main body 1, and an unillustrated subject is put on the top plate 60A.

2. Configuration of Photodetecting Unit

Figure 2:
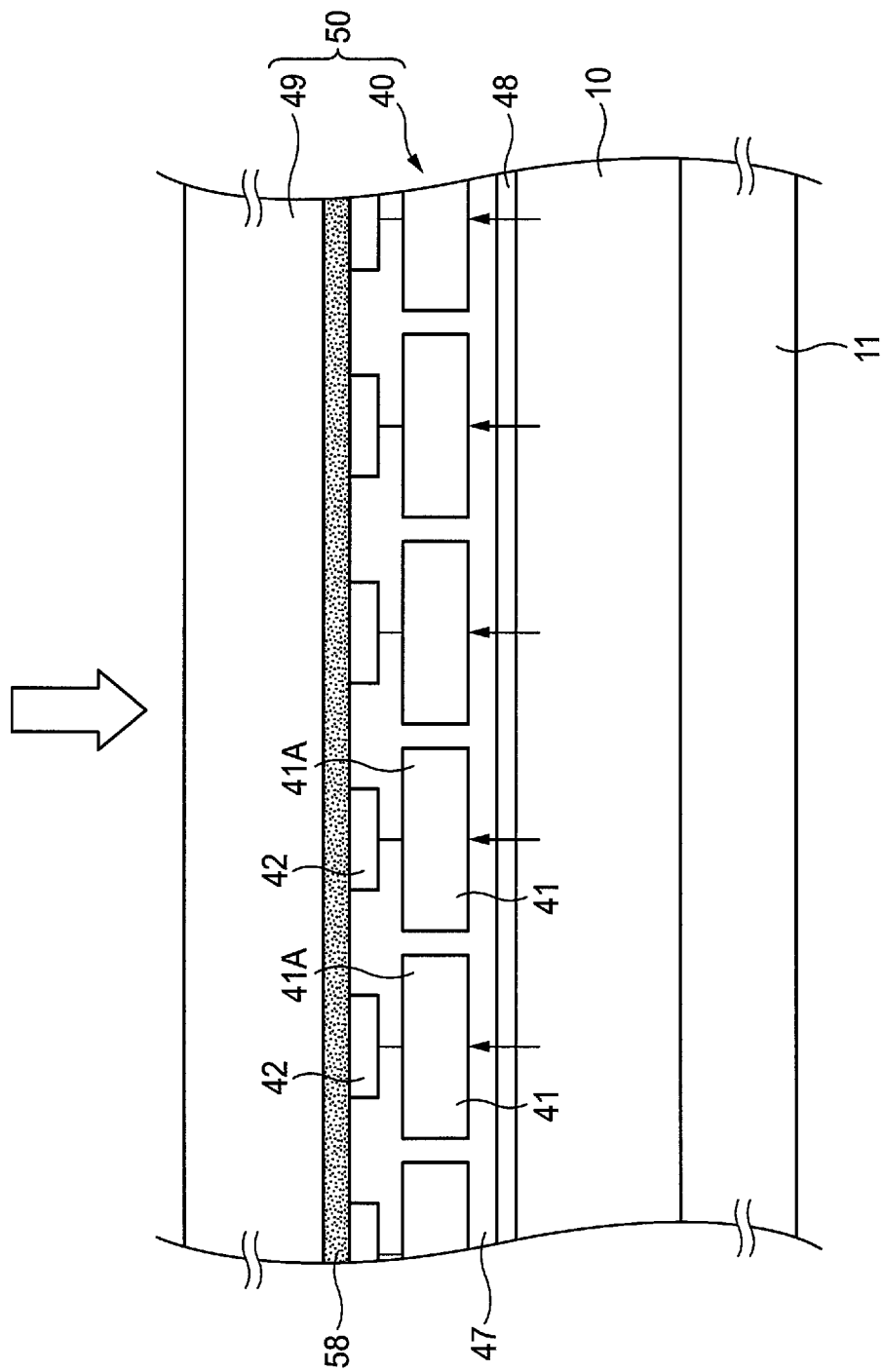
FIG. 2 is a side cross sectional view schematically showing a general configuration of a photodetecting unit.
Figure 3:
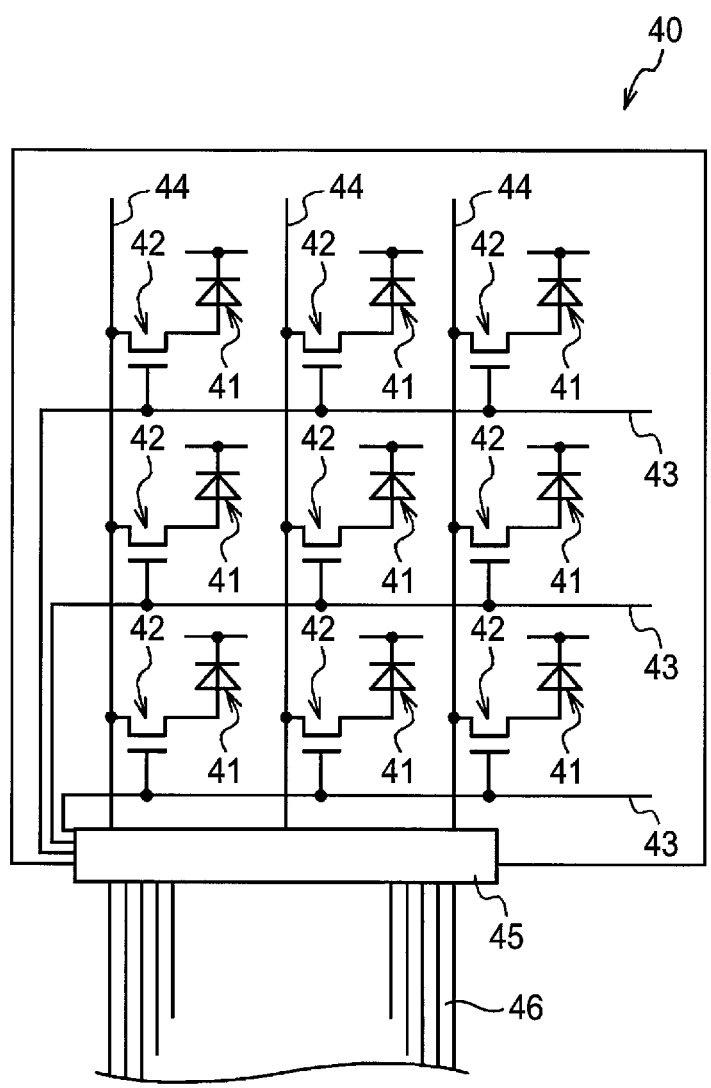
FIG. 3 is a plan view schematically showing a configuration of the photodetecting unit.

FIG. 2 is a side cross sectional view schematically showing the photodetecting unit 50. FIG. 3 is a plan view schematically showing a configuration of the photodetecting unit 50 in which elements are arranged in a two dimensional layout.

The photodetecting unit 50 has a thin film portion 40 whose one side faces the scintillator 10 and a plate-shaped reinforcing member 49 disposed on the other side of the thin film portion 40. The thin film portion 40 and the reinforcing member 49 are bonded together by way of an adhesive layer 58. The adhesive layer 58 does not always need to be placed over, in their entirety, the join plane between the thin film portion 40 and the reinforcing member 49. However, the adhesive layer 58 requires a joint area substantially sufficient for preventing the adhesive layer from becoming deflected under the weight of the scintillator 10.

Means for joining the reinforcing member 49 to the thin film portion 40 is not limited to bonding that employs an adhesive and includes other appropriate means, such as pressure bonding and welding. Descriptions are hereunder provided by reference to an example in which the reinforcing member and the thin film portion are joined by way of the adhesive layer that works as joining means. Bonding is illustrated as an example even in connection with means for joining the top plate 60A and the reinforcing member 49, which will be described later. However, the bonding means is not limited to lamination, and appropriate bonding means, such as pressure welding and welding, can also be adopted.

(Configuration of the Thin Film Portion)

The thin film portion 40 includes PDs (Photodiode) 41 made of a-Si, or the like, and TFTs 42 that are thin film switching elements made of a-Si, or the like. As shown in FIG. 2, the PDs 41 and the TFTs 42 are respectively stacked one on top of the other in a thicknesswise direction of the photodetecting unit 50.

The PD 41 has a photoconductive layer that converts the light (designated by an arrowhead solid line in FIG. 2), which has entered by way of the scintillator 10, into electric charges. Each of the PDs 41 is arranged so as to correspond to a pixel of an image detected by the photodetecting unit 50.

As shown in FIG. 3, each of the PDs 41 is equipped with the TFT 42, a gate line 43, and a data line 44. The respective gate lines 43 and the respective data lines 44 are extended to a connection terminal 45 and further connected to a circuit board of the control module 19 by way of flexible wiring 46, like an anisotropic conductive film connected to the connection terminal 45. The respective TFTs 42 are switched ON and OFF on a per-column basis by means of a control signal transmitted from a control block implemented on the circuit board by way of the gate lines 43. By way of the data lines 44, a signal processing block on the circuit board reads, as image signals, electric charges in the respective PDs 41 whose corresponding TFTs 42 remain in an ON position. The electric charges in the respective PDs 41 are sequentially read on a per-column basis, whereby a two-dimensional image is detected.

In FIG. 2, both sides of the photodetecting unit 50 in its thicknesswise direction are made smooth by means of a planarizing layer (a film made of a resin) 47. It is preferable to provide the photodetecting unit 50 with the planarizing layer 47. However, the planarizing layer 47 may also be omitted.

The photodetecting unit 50 is bonded to the scintillator 10 by way of an adhesive layer 48.

Neither the adhesive layer 48 nor the planarizing layer 47 may be interposed between the scintillator 10 and the photodetecting unit 50. The scintillator 10 may also be pressed against and brought into close, direct contact with the surface of the photodetecting unit 50.

In relation to a resin that makes up the planarizing layer and the adhesive layer interposed between the photodetecting unit 50 and the scintillator 10 and a resin layer which is a transparent liquid or gel making up a matching oil layer, specific restrictions are not imposed on the resin, so long as the resin enables scintillation light emitted from the scintillator 10 to arrive at the photodetecting unit 50 without undergoing substantial attenuation.

Polyimide, parylene, or the like, can be used as a resin that makes up the planarizing layer, and polyimide that exhibits ease of film formation is preferable.

A preferable adhesive to be used for making up the adhesive layer is one that exhibits optical transparency to the scintillation light emitted from the scintillator 10; for instance, a thermoplastic resin, a UV curable adhesive, a heat curing adhesive, a room-temperature curing adhesive, a two-sided adhesive substrate, and the like. From the viewpoint of prevention of deterioration of a degree of image sharpness, using an adhesive made of a low-viscosity epoxy resin is preferable because the epoxy resin can form an adhesive layer that is sufficiently thin with respect to a pixel size of the photodetecting unit 50.

A thickness of an adhesive layer made of a resin, such as a planarizing layer and an adhesive layer is preferably 50 micrometers or less from the viewpoint of sensitivity and image quality. More preferably, the thickness falls within a range from 5 micrometers to 30 micrometers.

(A Configuration of the Reinforcing Member)

The reinforcing member 49 is disposed on the X-ray entrance side of the thin film portion 40. The reinforcing member 49 is made of a low X-ray absorbent material that exhibits an X-ray absorbency which is lower than that exhibited by a glass material and that is lower than a substrate 51 to be described later in terms of the X-ray absorbency. An aluminum equivalent of the reinforcing member 49 with respect to X radiation generated by a tube voltage of 60 kV is under 1.8 mm.

Here, the aluminum equivalent is an index that shows a thickness of an aluminum plate (purity 99% or more) achieved when the X-ray absorbency is compared with transparency of aluminum. When the aluminum equivalent is measured, a member that is a test target is typically placed at a position spaced apart from the X-ray source by 1 to 2 meters, and the quantity of X radiation passed through the member is measured without involvement of an obstacle between the X-ray source and the member. Depending on a usage condition of the X-ray image detection apparatus, another member that absorbs X radiation is conceived to be placed on the X-ray entrance side of the reinforcing member 49. Therefore, the aluminum equivalent of the reinforcing member 49 (at a tube voltage of 60 kV) is preferably 1.0 mm or less in consideration of a total quantity of X radiation absorbed by the member and the reinforcing member 49.

In the meantime, the reinforcing member 49 is for supporting the thin film portion 40 and hence requires given strength. Allowing for this point and the reduction in an exposure dose of the subject, a preferable aluminum equivalent of the reinforcing member 49 against X radiation generated at a tube voltage of 60 kV preferably ranges from 0.1 mm to 1.0 mm.

Although the X-ray absorbing capacity of the reinforcing member is herein defined as an aluminum equivalent against X radiation generated at a tube voltage of 60 kV as mentioned above, it goes without saying that an aluminum equivalent against X radiation generated at a tube voltage other than 60 kV (e.g., 80 kV) can be calculated from the aluminum equivalent acquired under the aforementioned requirements. Absorbency of X radiation can be tested in conformance with the standards of JESRA (Japan Engineering Standards for Radiation Apparatus). For instance, measurement of an aluminum equivalent can also be performed at 80 kV, 2 mA, and 40 sec. that are analogous to the requirements stipulated by JESRA.

Moreover, when the X-ray imaging cassette is made as a result of the main body 1 being accommodated in the housing 60 as shown in FIG. 1, an aluminum equivalent (a tube voltage of 60 kV) achieved when both the top plate 60A of the housing 60 and the reinforcing member 49 are used is preferably under 1.8 mm. More preferably, the aluminum equivalent ranges from 0.1 mm to 1.0 mm. The aluminum equivalent (at a tube voltage of 60 kV) achieved when both the top plate 60A of the housing 60 and the reinforcing member 49 are used may be measured on the basis of the quantity of X radiation achieved after X radiation emitted from the X-ray source has passed through the top plate 60A and the reinforcing member 49 in sequence while the top plate 60A and the reinforcing member 49 remain stacked one on top of the other. Alternatively, the aluminum equivalent achieved by means of the top plate 60A and the aluminum equivalent achieved by means of the reinforcing member 49 may be separately measured, and a total of measurement values may also be determined.

The aluminum equivalent achieved by means of the reinforcing member 49 and the aluminum equivalent achieved by means of the top plate 60A are respectively determined in consideration of energy of X radiation applied. In the case of; for instance, mammographic applications, the energy of X radiation applied is usually as low as 28 keV or thereabouts. When compared with a case where X radiation having a higher energy is applied, it is preferable that the aluminum equivalent of the reinforcing member 49 and that of the top plate 60A be set to a relatively lower value.

As long as the aluminum equivalent of the reinforcing member 49 against X radiation generated at a tube voltage of 60 kV is under 1.8 mm, any specific limitations are not imposed on a low X-radiation absorbent material used for making up the reinforcing member 49. However, using metal (including a metallic compound and an alloy) and/or a resin is preferable. Preferable metal includes at least one of single metals, such as Al, Mg, Cr, Zr, Ti, and Mn, oxides thereof, and metal alloys of thereof. Corrosion resistance of the thin film portion 40 can be enhanced by employing at least any one of Mg, Cr, Zr, Ti, and Mn as a metallic material of the reinforcing member 49. Corrosion resistance of the thin film portion 40 can be enhanced by using for the reinforcing member 49 an aluminum alloy including at least any one of; for instance, Mg, Cr, Zr, Ti, and Mn. Alumina ($Al_2O_3$), or the like, is formed over a surface of the aluminum alloy by means of surface treatment of such an aluminum alloy, whereby corrosion resistance of the thin film portion 40 can be enhanced still further.

A preferable resin is at least one of polyimide, polyethylene naphthalate, polystyrene, and aramid (all aromatic polyamides). Single resin films that can be used for the reinforcing member 49 include; for instance, a transparent polyimide film, a polyallylate (PAR) film, an OPS (registered trademark) film (a polystyrene film), an aramid film, and the like. All of these films yield an advantage of a low X-ray absorbency and high heat resistance. Products manufactured by Tosoh Corporation and products manufactured by Asahikasei Chemicals Corporation are referred to as the OPS film, and these films exhibit an advantage of superior mechanical strength (stiffness) and low water absorption. Superior mechanical strength is advantageous to support the thin film portion 40 after peeling of the substrate 51. Moreover, low water absorption is advantageous to prevent corrosion and deterioration of the thin film portion 40 and the scintillator 10.

In relation to a heatresistant temperature of the reinforcing member 49, the transparent polyimide film has a heatresistant temperature of about 300 degrees centigrade; the polyallylate film has a heatresistant temperature of about 175 degrees centigrade; the OPS film has a heatresistant temperature of about 250 degrees centigrade; and the aramid film has a heatresistant temperature of about 200 degrees centigrade or more. These high heatresistant temperatures are particularly effective in a case (see FIG. 15) where the scintillator is deposited on the reinforcing member 49.

Figure 12:
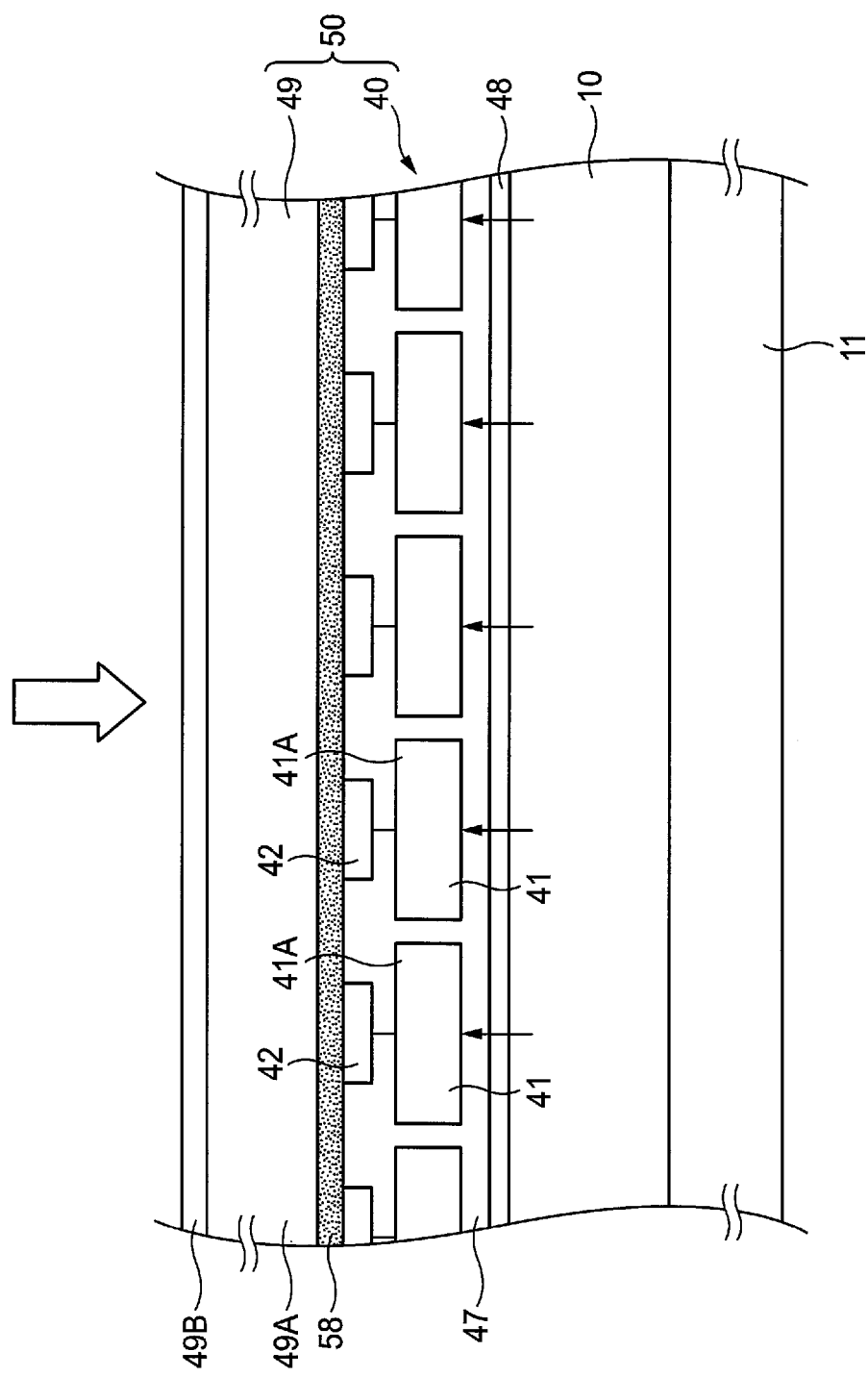
FIG. 12 is a side cross sectional view showing an example modification of the reinforcing member.

The reinforcing member 49 can be formed from only metal or a resin or a combined use of metal and a resin, like a resin including dispersed metal particles. Further, the reinforcing member 49 may be formed into a single layer or two or more layers as illustrated in FIG. 12. Furthermore, the reinforcing member 49 is preferably a light reflecting member that reflects fluorescence emitted from the scintillator 10.

Depending on a low X-ray absorbent material making up the reinforcing member 49, a preferable thickness of the reinforcing member 49 usually ranges from 0.01 mm to 1 mm. So long as the thickness of the reinforcing member 49 is made smaller than the thickness of the substrate 51 to be described later, the distance between the subject placed on the top plate 60A and the thin film portion 40 can be made shorter, so that higher image quality can be promoted.

Incidentally, the reinforcing member 49 is placed on a peeled surface of the thin film portion 40 formed as a result of the thin film portion 40 being peeled off from the substrate 51 (FIG. 7) after formation of the thin film portion 40 on the substrate 51 in a process for manufacturing the X-ray imaging cassette 100 to be described later. As a result of peeling of the substrate 51, the quantity of X radiation entering the scintillator 10 increases. In a state where the substrate 51 remains peeled, the thin film portion 40 is supported by the reinforcing member 49.

The substrate 51 is an ancillary member for making up the reinforcing member 49 and is to be peeled at some stage. For this reason, as a matter of course, a material of the substrate 51 can be appropriately determined without taking into account X-ray absorption. As a result of peeling of the substrate 51, the thus-removed substrate 51 can be recycled, which leads to cost cutting.

The thin film portion 40 can be reinforced by provision of the reinforcing member 49 while the effect of reduction of X-ray absorption is accomplished by peeling off the substrate. The photodetecting unit 50 is integrated with the top plate 60A as a result of the reinforcing member 49 being bonded to the back side of the top plate 60A. At this time, the deflection of the X-ray image detection panel P10 owing to the weight of the scintillator 10 can be diminished as a result of the thin film portion 40 being reinforced by the reinforcing member 49. Accordingly, the X-ray image detection panel P10 and the top plate 60A are brought into close contact with each other along a laminate plane without involvement of any substantial clearance. Therefore, a damage to the scintillator 10, or the like, which would otherwise be caused when the X-ray image detection panel P10 collides against the top plate 60A when undergone impact, can be prevented, so that impact resistance of the scintillator 10 can be enhanced.

Since the reinforcing member 49 is provided, the reinforcing member 49 does not need to be firmly bonded, substantially in its entirety, to the top plate 60A in order to prevent occurrence of deflection. For this reason, only a portion of the surface of the reinforcing member 49 facing the top plate 60A (an outer periphery of the reinforcing member 49 shown in FIG. 1) is bonded to the top plate 60A by way of an adhesive layer 18. When compared with a configuration in which the reinforcing member 49 and the top plate 60A are bonded together substantially in their entirety, bonding strength (laminating strength) is lowered because of a difference in joint area between the configurations. As a result, the bonding strength between the reinforcing member 49 and the thin film portion 40 is greater than the bonding strength between the reinforcing member 49 and the top plate 60A. An adhesive having single adhesive force can be used for the adhesive layer 18 between the reinforcing member 49 and the top plate 60A and the adhesive layer 58 between the reinforcing member 49 and the thin film portion 40.

FIG. 1 that is a schematic diagram illustrates that clearance equivalent to the thickness of the adhesive layer 18 exists between the top plate 60A and the reinforcing member 49. However, the thickness of the adhesive layer 18 is not more than 100 micrometers (typically tens of micrometers); hence, clearance that allows occurrence of rattling (relative movement) between the top plate 60A and the reinforcing member 49 when the X-ray imaging cassette 100 has undergoes impact does not exist between the reinforcing member 49 and the top plate 60A. Specifically, the top plate 60A and the reinforcing member 49 remain in close contact with each other while substantial clearance does not exist along the laminate plane.

Incidentally, when the top plate 60A and the photodetecting unit 50 are separated from each other during replacement of the top plate 60A, the reinforcing member 49 is peeled off from the top plate 60A. At this time, the reinforcing member 49 is interposed between the thin film portion 40 and the top plate 60A, the top plate 60A and the photodetecting unit 50 can readily be separated from each other without inflicting a damage to the thin film portion 40 when compared with the case where the thin film portion 40 and the top plate 60A are bonded together. In addition, the bonding strength between the reinforcing member 49 and the thin film portion 40 is greater than the bonding strength between the reinforcing member 49 and the top plate 60A. Hence, a damage to the thin film portion 40, which would otherwise be inflicted as a result of the thin film portion 40 being separated from the reinforcing member 49 during separation of the top plate 60A from the photodetecting unit 50, is prevented, so that the top plate 60A and the photodetecting unit 50 can be separated from each other more easily.

Although the reinforcing member 49 can be provided every several pixels, laying the reinforcing member 49 over the entire surface of the thin film portion 40 in an integrated fashion is desirable from the viewpoint of reinforcement.

As mentioned above, light metal, such as aluminum, or a resin can be used as a material of the reinforcing member 49. When the reinforcing member 49 is made of aluminum and acts as a light reflection member, the light entered the reinforcing member 49 by way of the PDs 41 can be reflected toward the PDs 41 by means of the reinforcing member 49. The quantity of light entering the PDs 41 is resultantly increased, whereby detection sensitivity can be enhanced.

In order to reflect toward the thin film portion 40 the light reached the substrate 51 after having passed through the thin film portion 40 when the substrate 51 is not peeled off from the thin film portion 40, a conceivable way is to provide a reflection film, or the like, on the other side of the substrate 51 with respect to its side facing the thin film portion 40. However, reflecting the light by way of the substrate 51 is less preferable, because it entails great scattering of light, which would cause blurring of an image. In contrast, in a configuration in which the substrate 51 is peeled off and where the reinforcing member 49 is provided as a reflection member on the thin film portion 40, the thickness of the adhesive layer 18 used for bonding the thin film portion 40 to the reinforcing member 49 is 100 micrometers or less (typically tens of micrometers). When compared with a case where the substrate 51 typically having a thickness of 0.7 mm is present, X radiation absorption can be significantly diminished. For these reasons, in the configuration in which the substrate 51 is peeled off and in which the reinforcing member 49 is used in place of the substrate 51, it is preferable to make up the reinforcing member 49 as a reflection member.

When metal, such as aluminum, is used for the reinforcing member 49 for the purpose of forming the reinforcing member 49 as a reflection member, a metallic member is higher than a glass substrate in terms of thermal conductivity. Hence, unevenness in image, which would otherwise be caused by propagation of heat from the subject to the photodetecting unit 50, can be prevented. Specifically, thermal unevenness (heat unevenness) in a glass member supporting the photodetecting unit would cause unevenness in temperature of the PDs 41 in an image formation region, which would in turn cause unevenness in performance. For these reasons, a metallic member exhibiting superior thermal conductivity is employed as a reinforcing member, whereby image quality can be enhanced.

When the reinforcing member 49 is made of single metal, like aluminum, or its alloy, the reinforcing member 49 exhibits a high effect of sealing the thin film portion 40. Specifically, airtightness and watertightness of the thin film portion 40 become easy to assure by use of such a reinforcing member 49. Accordingly, deterioration of performance of the scintillator 10, which would otherwise be caused by moisture absorption, can be sufficiently prevented.

3. Configuration of Scintillator

The scintillator 10 is deposited on a support 11 that is made of a material, such as aluminum, which reflects light. The support 11 is not restricted to a plate made of aluminum. Any material for the support 11 can be appropriately selected from a carbon plate, CFRP (Carbon Fiber Reinforced Plastic), a glass plate, a quartz plate, a sapphire plate, and others. The support 11 is not limited particularly to these plates, so long as a scintillator is formed over the surface of the support. However, when the support 11 doubles also as a light reflection member, it is better to use light metal, such as aluminum, for a material of the support. Since the support 11 is placed on the other side of the main body 1 with respect to its X-ray entrance side, the support 11 can be formed from a material that exhibits low X-ray transmissivity.

Here, the support 11 is not indispensable for the main body 1. Specifically, after a scintillator has been formed and deposited over the support 11, the scintillator can be used while peeled off from the support 11. A light reflection member can also be provided on the other side of the scintillator 10 with respect to its side facing the photodetecting unit 50.

The scintillator 10 is covered with a protective film 30 made of parylene, or the like. The protective film 30 is formed by means of a vapor phase deposition technique and seals the scintillator 10 on the support 11. The protective film made of parylene by means of vapor phase deposition exhibits superior flexibility as well as superior adhesion with respect to the scintillator 10. Hence, the protective film exhibits superior followability to warpage, or the like, in the support 11 and the reinforcing member 49.

So long as the scintillator is protected from moisture by another means, such as wrapping the scintillator 10 with a damp-proof film in an airtight and watertight manner, the protective film 30 may be omitted.

The scintillator 10 is made up of a group of columnar crystals formed by letting a fluorescent material grow into a columnar shape, CsI:Tl (thallium activated cesium iodide) is used as a fluorescent material. In addition, NaI:Tl (thallium activated sodium iodide), CsI:Na (sodium activated cesium iodide), or the like, can also be used as a fluorescent material for the scintillator 10. Using CsI:Tl for a material is preferable in that a luminescence emission spectrum conforms to a local maximum value (around 550 nm) of spectrum sensitivity of an a-Si photodiode.

It is also possible that the scintillator 10 will not include any columnar crystals. Further, the scintillator can also be formed by coating the support with; for instance, GOS [$Gd_2O_2S$:Tb (terbium activated gadolinium oxysulfide)].

Now, it is desirable that the scintillator 10 be formed by means of vapor phase deposition. A general description of vapor phase deposition is as follows. Namely, CsI that is a base material is heated in a resistance heating crucible in an environment, or at a vacuum degree of 0.01 to 10 Pa, by means, like energization, until CsI is evaporated. Likewise, Tl serving as an activator is heated in the resistance heating crucible in the environment, or at a vacuum degree of 0.01 to 10 Pa, by means, like energization, until Tl is evaporated. The temperature of the support 11 is set to a room temperature (20 degrees centigrade) to 300 degrees centigrade, whereby CsI:Tl is deposited on the support 11. A shape, size, and porosity of the crystal of the scintillator 10 can be controlled by changing the degree of vacuum, the temperature of the support, a deposition rate, or the like.

Figure 4:
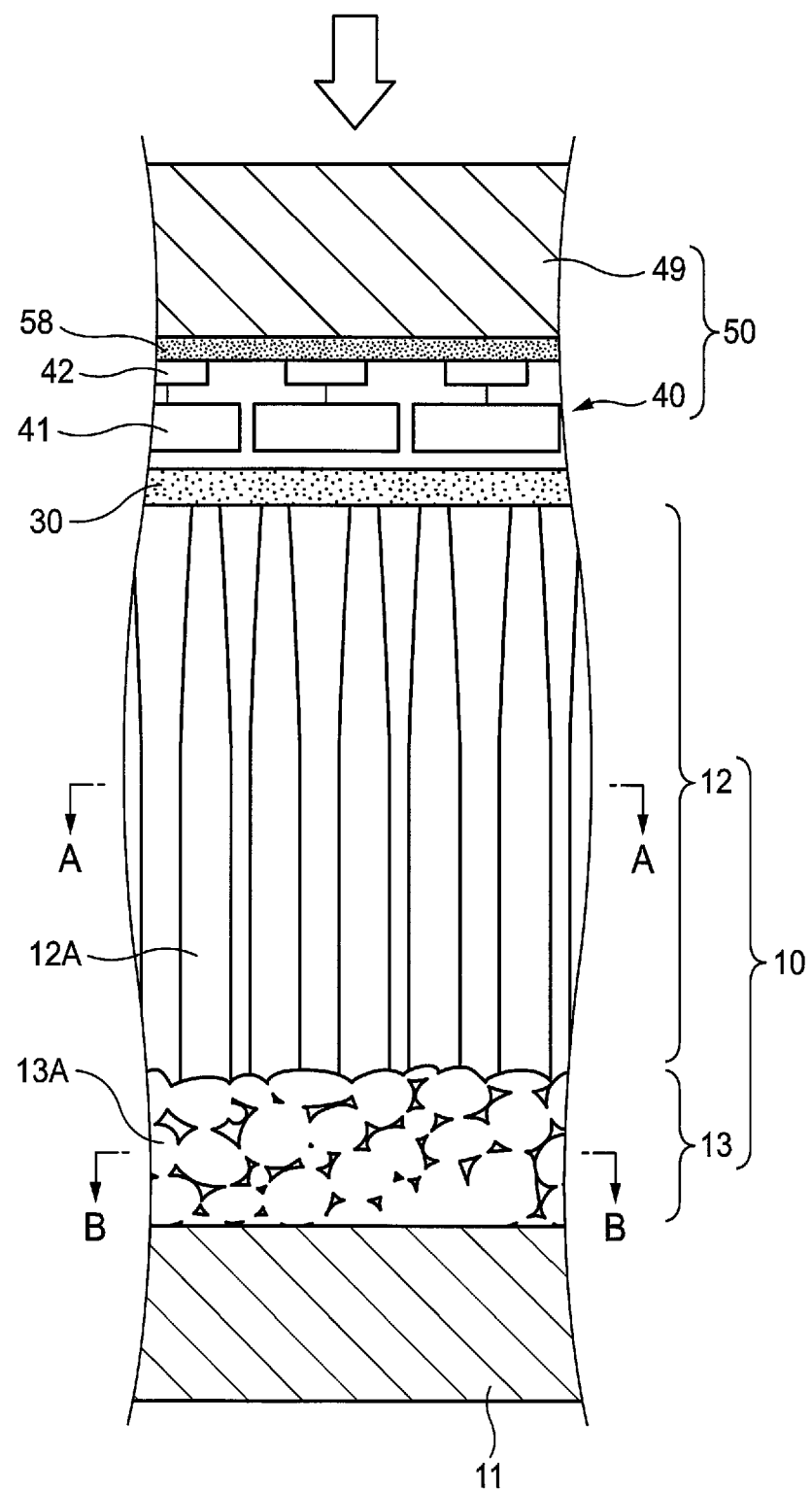
FIG. 4 is a side cross sectional view schematically showing a crystalline structure of a scintillator.

FIG. 4 is a side cross sectional view schematically showing a crystalline structure of the scintillator 10. The scintillator 10 includes a columnar portion 12 formed from a group of columnar crystals 12A and a non-columnar portion 13 including non-columnar crystals 13A formed at a base end of the columnar crystals 12A.

Fluorescent emitted from the scintillator 10 when the scintillator is exposed to X radiation is guided by the columnar crystal 12A in its heightwise direction (a direction of crystal growth), to thus enter the photodetecting unit 50. The light propagated toward the support 11 is, at this time, reflected by the non-columnar portion 13 and the support 11, thereby entering the photodetecting unit 50.

[Configuration of Columnar Portion]

The columnar portion 12 is an aggregate of the plurality of columnar crystals 12A. In the example shown in FIG. 4, the respective columnar crystals 12A stand substantially upright on the support 11. Leading ends of the columnar crystals 12A are formed into a pinched shape. The leading ends of the respective columnar crystals 12A can also be abraded. The plurality of columnar crystals 12A oppose one pixel (one PD 41) of the photodetecting unit 50.

The columnar crystals 12A are superior to non-columnar crystals in terms of a crystalline property and emit larger quantities of fluorescence. The columnar crystals 12A adjoining each other by way of voids stand upright in the thicknesswise direction of the scintillator; accordingly, the columnar crystals 12A act as a light guide, to thus guide light in a heightwise direction of the columns. Since the light guide effect of the columnar crystals 12A prevents scattering of light, which would arise among the pixels, a detected image can be made sharp.

Figure 5:
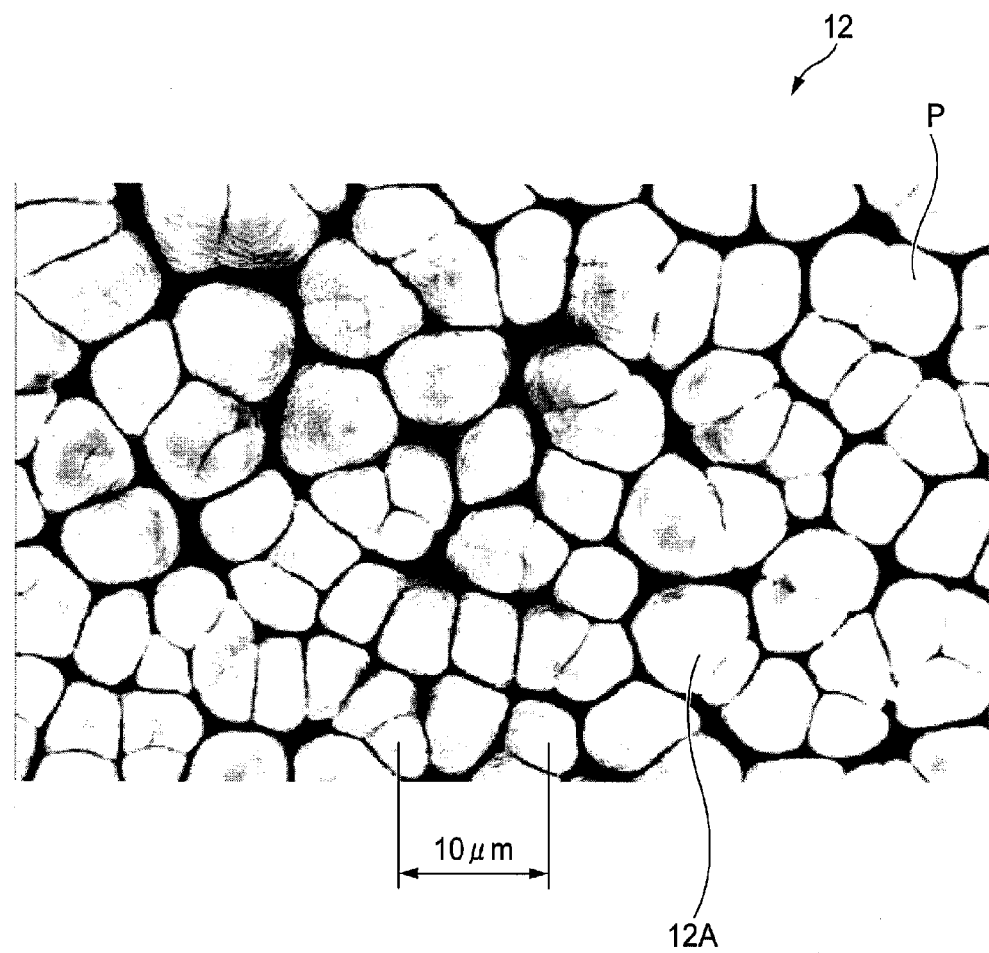
FIG. 5 is an electron microscope photograph (an SEM image) showing a cross section of a columnar crystal.

FIG. 5 is an electron microscope photograph showing the columnar portion 12 taken along cross section A-A shown in FIG. 4 (i.e., a cross section of the columnar portion 12 achieved at substantially a center in its heightwise direction). Voids (looked densely in FIG. 5) exist among the adjacent columnar crystals 12A. The columnar crystals 12A have a substantially uniform cross-sectional diameter with respect to the direction of crystal growth. The adjacent columnar crystals 12A join to each other in a part of an area of the columnar portion 12, thereby making up an integrated columnar body (see; for instance, reference symbol P in FIG. 5).

In consideration of X-ray absorbing capacity commensurate with required sensitivity, the thickness of the columnar portion 12 is set to a value of about 200 micrometers for mammographic applications and a value of 500 micrometers or more for general photographing. However, when the columnar portion 12 is too thick, the usage efficiency of fluorescence will be likely to decrease because of light absorption or scattering. For this reason, the thickness of the columnar portion 12 is set to an appropriate value in consideration of sensitivity and the usage efficiency of fluorescence.

[Configuration of Non-Columnar Portion]

The non-columnar portion 13 includes substantially spherical or indefinite-form non-columnar crystals 13A. The non-columnar portion 13 often includes an amorphous (non-crystalline) portions.

A preferable shape of the non-columnar crystals 13A is a substantially spherical shape in terms of voids being easily held among crystals and the capability of enhancing reflection efficiency. Specifically, it is preferable that the non-columnar portion 13 will be formed from an aggregate of substantially spherical crystals (the non-columnar crystals 13A that are substantially spherical crystals).

Figure 6:
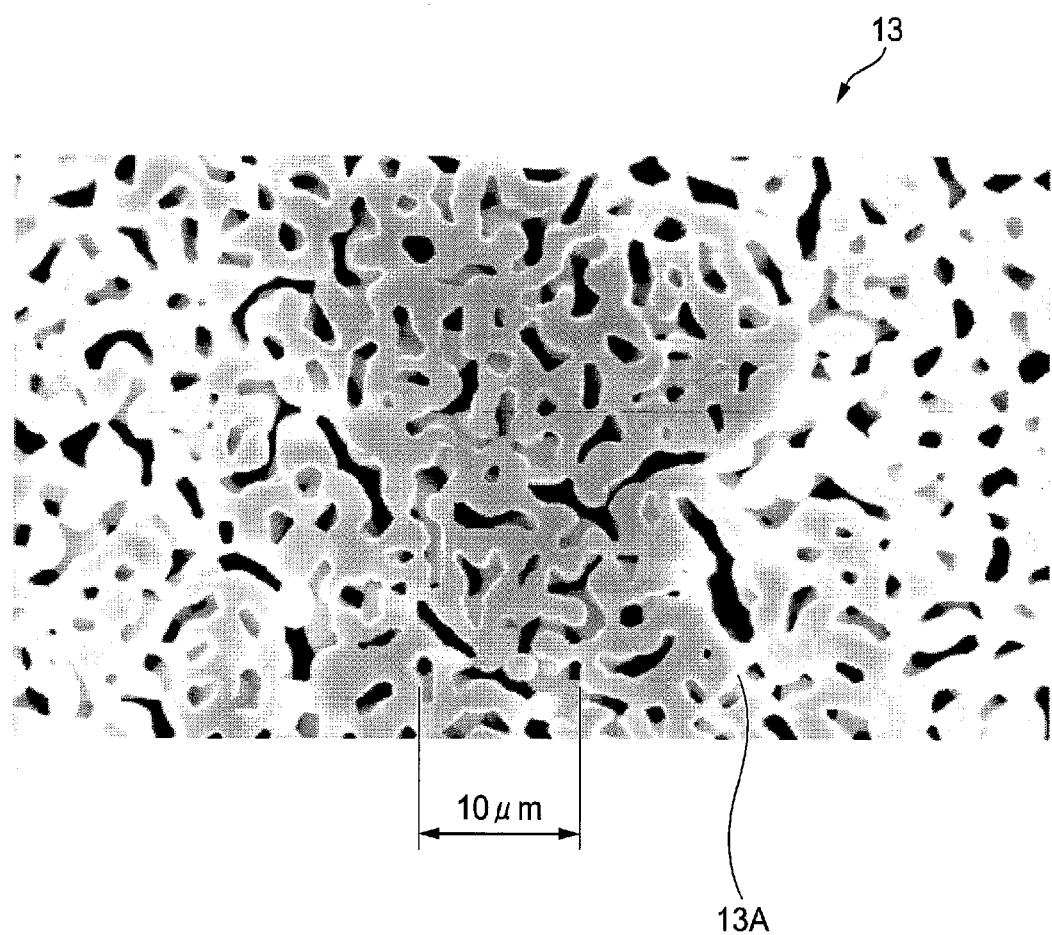
FIG. 6 is an electron microscope photograph (an SEM image) showing a cross section of a non-columnar crystal.

FIG. 6 is an electron microscope photograph of the non-columnar portion 13 taken along cross section B-B shown in FIG. 4 (a cross section of a base end side of the non-columnar portion 13 taken in its thicknesswise direction). In the non-columnar portion 13, the non-columnar crystals 13A that are smaller than the columnar crystals 12A shown in FIG. 5 in terms of a diameter irregularly join and overlap each other. Very few definite voids among the crystals are observed. The voids shown in FIG. 6 are smaller in number than those shown in FIG. 5. Observation results shown in FIGS. 5 and 6 clearly show that the porosity of the non-columnar portion 13 is lower than the porosity of the columnar portion 12.

The porosity of the non-columnar portion 13 is calculated from a deposition area of the non-columnar portion 13 on the support 11, the thickness of the non-columnar portion 13, CsI density, and an actually measured weight of the scintillator panel. The thus-calculated porosity of the non-columnar portion 13 achieved in its entirety along its thicknesswise direction is 10% or less.

The non-columnar portion 13 is an area formed over the support 11 in an initial phase of deposition. The porosity of an area of the non-columnar portion 13 contacting the surface of the support 11 is zero or nearly zero. The base end of the non-columnar portion 13 remains in close contact, along an entire contact plane, with the support 11.

The thickness of the non-columnar portion 13 is smaller than the thickness of the columnar portion 12 and preferably ranges from 5 micrometers to 125 micrometers. Specifically, in order to assure adhesion to the support 11, the thickness of the non-columnar portion 13 should preferably be 5 micrometers or more. If the thickness of the non-columnar portion 13 that does not exhibit any light guide effect is too large, light crosses each other among pixels in the non-columnar portion 13, whereupon an image becomes likely to become blurred. For this reason, it is preferable that the thickness of the non-columnar portion 13 be less than 125 micrometers.

Moreover, a sufficient thickness of the non-columnar portion 13 is a minimum value at which adhesion to the support 11 and a light reflection capability are accomplished.

Depending on manufacturing conditions, or the like, the non-columnar portion 13 may also be configured into a plurality of stacked layers rather than into a single layer. In such a case, the thickness of the non-columnar portion 13 refers to a distance from the surface of the support 11 to the topmost surface of the non-columnar portion 13.

In relation to measurement of a crystal diameter achieved when the crystals remain adhered to each other, as in the case of the non-columnar portion 13, a line interconnecting indentations (recesses) existing between the adjoining non-columnar crystals 13A is taken as a grain boundary. The crystals remaining adhered to each other are separated from each other in such a way that the minimum polygon is formed, and the diameters of the crystals are measured. As in the case of the diameters of the columnar crystals 12A of the columnar portion 12, an average of the measured crystal diameters is determined, and the average is adopted.

From the viewpoint of an efficient reflection property and adhesion to the support 11, a preferable diameter of the non-columnar crystals 13A of the non-columnar portion 13 ranges from 0.5 micrometers to 7.0 micrometers. The diameter of the non-columnar crystals 13A is smaller than the diameter of the columnar crystals 12A.

Since the substantially spherical shape of the crystals is easily maintained, a smaller diameter is preferable for the non-columnar crystals 13A. However, if the diameter of the non-columnar crystals 13A is too small, the porosity will come close to zero, and the non-columnar portion 13 will not play the role of the light reflection layer. For this reason, a preferable diameter of the non-columnar crystals 13A is 0.5 micrometers or more. On the contrary, if the diameter of the non-columnar crystals 13A is too large, flatness and a surface area of the non-columnar portion 13 will decrease, which in turn may cause a decline of adhesion to the support 11. Further, the crystals will join each other to thereby decrease porosity and deteriorate a reflection effect. For these reasons, a preferable crystal diameter for the non-columnar portion 13 is 7.0 micrometers or less.

As a result of such a non-columnar portion 13 being formed, the columnar crystals 12A can be caused to grow in a superior crystalline state while taking the non-columnar portion 13 as a base. The diameter, thickness, and porosity of the non-columnar crystals 13A are determined in consideration of a light reflection characteristic and adhesion to the support 11.

Since adhesion between the support 11 and the scintillator 10 is enhanced by provision of the non-columnar portion 13, the scintillator 10 will become less likely to fall from the support 11 even when heat emitted from the control module 19 propagates to the scintillator 10.

For instance, an organic photoelectric conversion (OPC) material, an organic TFT, a TFT using an amorphous oxide (e.g., a-IGZO), and a flexible material (aramid, and a bio-nanofiber), or the like, can be used for the photodetecting unit 50 (including the reinforcing member 49), the support 11, and others. These device-related materials will be described later.

4. Method of Manufacturing X-Ray Imaging Cassette

An example method for manufacturing the cassette 100 having the foregoing configurations will now be described by reference to FIGS. 7 through 11.

Figure 7:
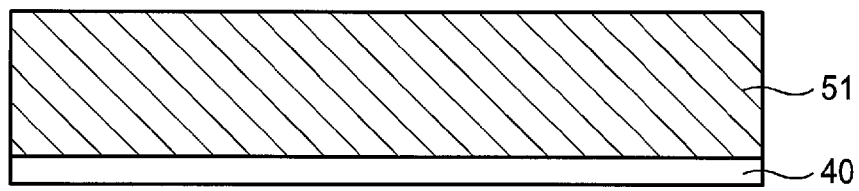
FIG. 7 is a side cross sectional view schematically showing a substrate and a thin film portion.

As shown in FIG. 7, the thin film portion 40 is formed over the substrate 51 made of alkaline free glass, or the like. When the thin film portion 40 is formed, the PDs 41 and the TFTs 42 (see FIG. 2) making up the thin film portion 40 are fabricated on the substrate 51 by use of a photolithography or etching process, or the like.

Since the substrate 51 is to be peeled off in a subsequent process and will not finally make up the photodetecting unit 50, there is no necessity for taking into account an X-ray absorption property for the substrate. Using the substrate 51 whose thickness is sufficient to assure ease of handling and removal in subsequent processes is preferable.

Figure 8:
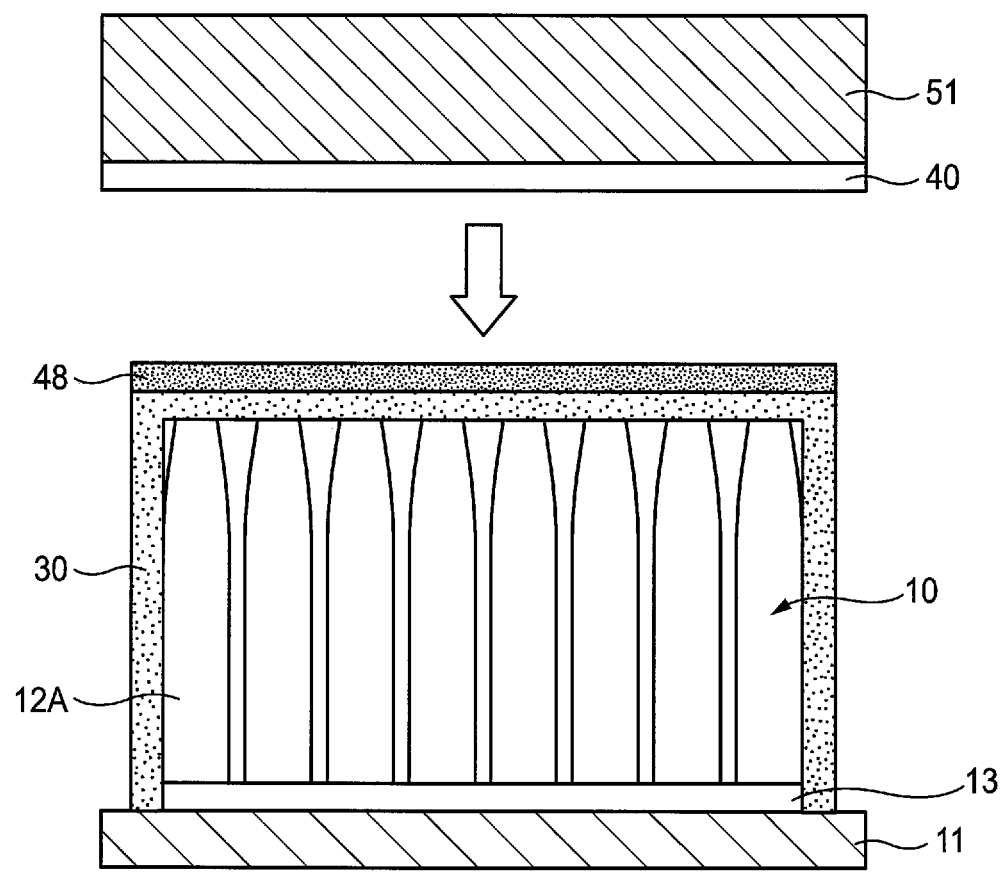
FIG. 8 is a side cross sectional view showing a process for bonding the substrate and the thin film portion shown in FIG. 7 to the scintillator deposited on a support.

As shown in FIG. 8, the substrate 51 and the thin film portion 40 are bonded to the separately produced scintillator 10 before removal of the substrate 51, and the thin film portion 40 and the scintillator 10 are uniformly brought into close contact with each other in an integrated fashion. When manufactured, the scintillator 10 is deposited on the support 11 and subsequently sealed to the same by formation of the protective film 30. The scintillator 10 and the thin film portion 40 both of which have been manufactured as mentioned above are bonded together while the adhesive layer 48 is sandwiched therebetween.

No specific limitations are imposed on the method for bringing the scintillator 10 and the thin film portion 40 into close contact with each other, and the essential requirement for the method is to optically couple the scintillator 10 to the thin film portion 40. Either a method for letting both the scintillator 10 and the thin film portion 40 directly oppose each other and bringing them into close contact with each other or a method for bringing them into close contact with each other while a resin layer is sandwiched therebetween may also be taken as the method for bringing the scintillator 10 and the thin film portion 40 into close contact with each other.

Figure 9:
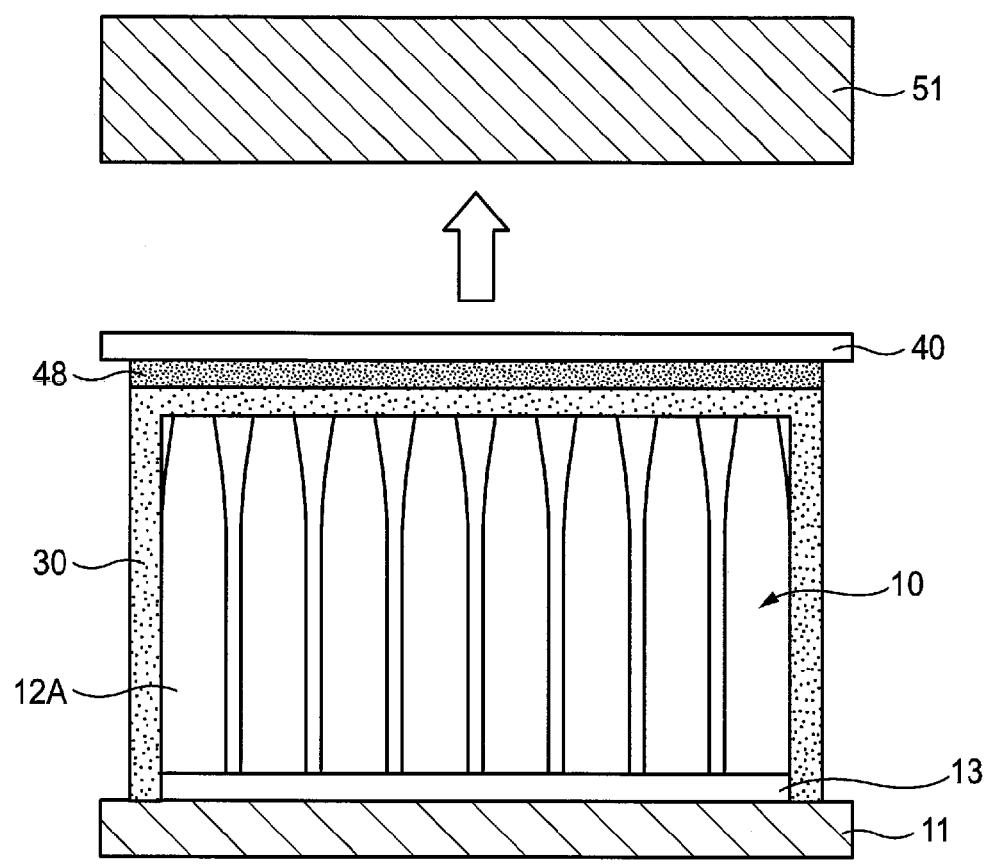
FIG. 9 is a side cross sectional view showing a process of peeling the substrate off from the thin film portion.

Next, the substrate 51 is peeled off from the thin film portion 40 as shown in FIG. 9. Since the thin film portion 40 is supported by means of the scintillator 10 and the support 11 on this occasion, ease of handling of the thin film portion 40 achieved during removal of the substrate 51 becomes superior. However, when the thin film portion 40 can be held by appropriate handling means, the scintillator 10 and the thin film portion 40 can also be integrated into one after the substrate 51 has been peeled off.

Figure 10:
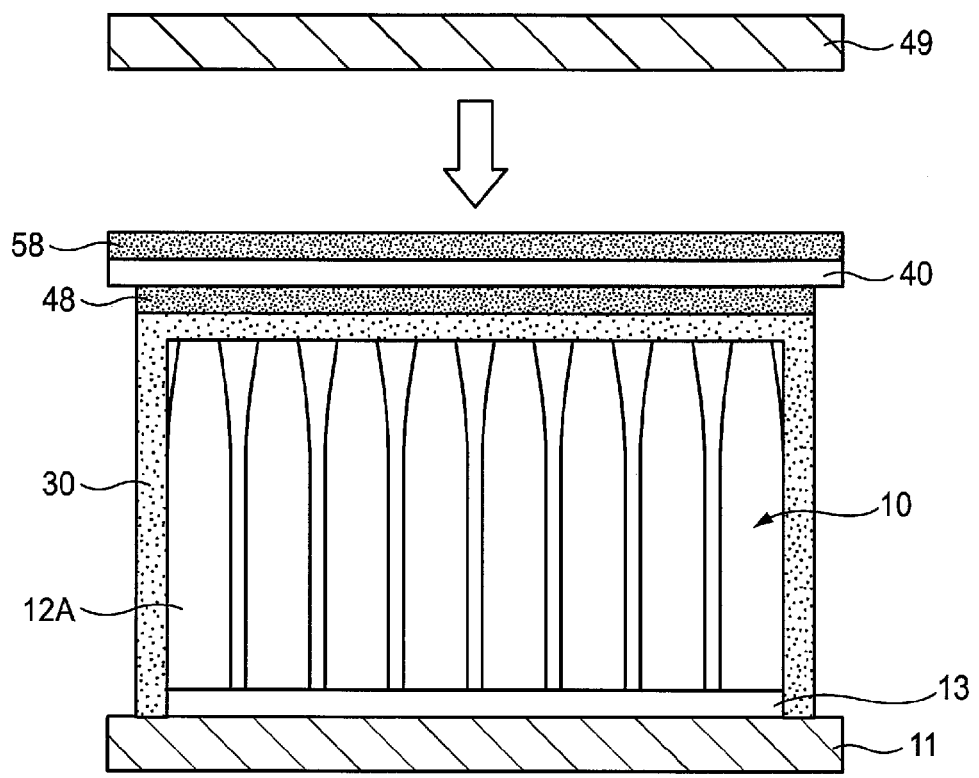
FIG. 10 is a side cross sectional view showing a process for providing the thin film portion with a reinforcing member.

As shown in FIG. 10, the reinforcing member 49 is next bonded to the surface of the thin film portion 40 from which the substrate 51 has been peeled off while the adhesive layer 58 is sandwiched therebetween. The X-ray image detection panel P10 into which the scintillator 10, the thin film portion 40, and the reinforcing member 49 are integrated is thus manufactured. The X-ray image detection panel P10 is assembled to the control module 19. The main body 1 is thereby manufactured.

Figure 11:
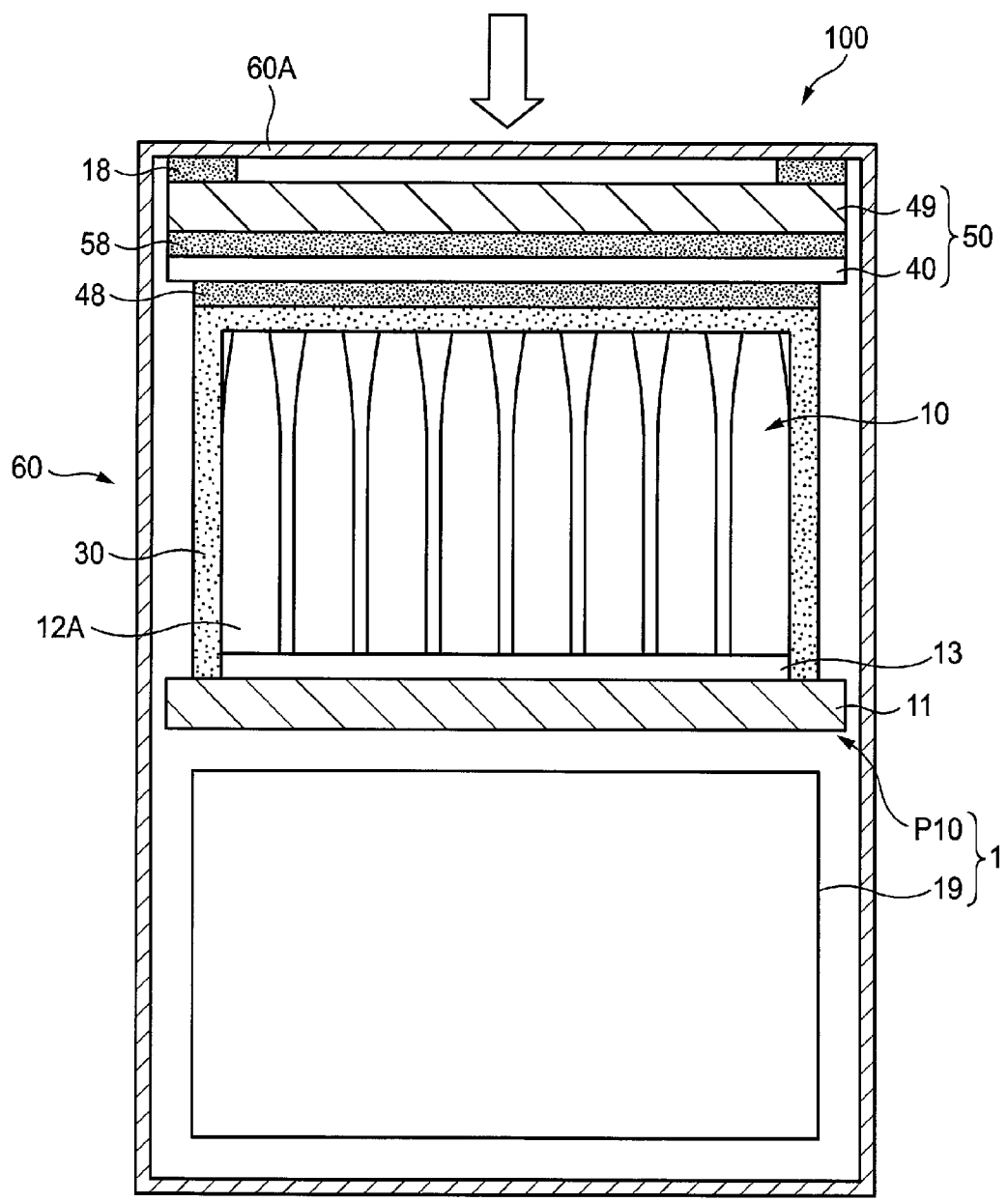
FIG. 11 is a side cross sectional view schematically showing an X-ray image detection apparatus built in a cassette housing.

As shown in FIG. 11, the main body 1 is then accommodated into the housing 60, and the reinforcing member 49 is bonded to the back side of the top plate 60A while the adhesive layer 18 is sandwiched therebetween. The load of the subject supported by the top plate 60A is received by the top plate 60A and the main body 1. Withstand load of the X-ray imaging cassette 100 can be increased by means of stacking the top plate 60A and the main body 1 in an integrated fashion as mentioned above.

The X-ray imaging cassette 100 is manufactured as mentioned above.

5. Working Effect of Reinforcing Member of Photodetecting Unit

The X-ray imaging cassette 100 having been described above yields the following working effects.

Since the thin film portion 40 is reinforced as mentioned above by the reinforcing member 49, clearance, which would otherwise arise between the panel P10 and the top plate 60A as a result of deflection of the panel P10, is prevented. Since the panel P10 and the top plate 60A are thus brought into close contact with each other, impact resistance of the panel P10 can be enhanced. Enhancement of impact resistance is particularly important for a portable cassette 100.

As a result of the reinforcing member 49 being sandwiched between the thin film portion 40 and the top plate 60A, it becomes easier to separate the photodetecting unit 50 from the top plate 60A without inflicting damage to the thin film portion 40 during replacement of the top plate 60A. In addition, even when the adhesive force exerted between the top plate 60A and the panel P10 is not increased, the top plate 60A and the panel P10 are brought into close contact with each other without involvement of any substantial clearance as a result of provision of the reinforcing member 49. Therefore, it becomes possible to obviate a necessity for bonding the top plate 60A to the photodetecting unit 50 in their entirety in a sense that the top plate 60A and the photodetecting unit 50 are firmly bonded together along the laminate plane existing therebetween. As a result, the adhesive force exerted between the top plate 60A and the reinforcing member 49 can be made smaller than the adhesive force exerted between the thin film portion 40 and the reinforcing member 49. Accordingly, during replacement of the top plate 60A, the photodetecting unit 50 can be easily peeled off from the top plate 60A without inflicting damage to the thin film portion 40. In other words, ease of rework achieved during replacement of the top plate 60A can be enhanced.

Resistance of the thin film portion 40 and the scintillator 10 to a moisture, or the like, in the open air is assured as a result of the thin film portion 40 being provided with the reinforcing member 49. Corrosion of the thin film portion 40 and deterioration of performance of the scintillator 10 can be prevented.

Since the reinforcing member 49 is provided to reinforce and protect the thin film portion 40 as mentioned above, a problem, which would otherwise arise as a result of the substrate 51 being peeled off from the photodetecting unit 50, is resolved. Accordingly, the effect of enhancement of picture quality yielded by the configuration in which the scintillator is exposed to X radiation applied in the direction of the photodetecting unit can be sufficiently accomplished. Further, the aluminum equivalent of the reinforcing member 49 is under 1.8 mm. Since X radiation absorption occurred on the X-ray entrance side of the scintillator 10 can be reduced to a minimum by use of such a reinforcing member 49 exhibiting low X radiation absorbency, image quality of a detected image can be enhanced by means of an increase in the quantity of X radiation entering the scintillator 10. It is therefore possible to achieve both a reduction in absorption of X radiation by the photodetecting unit and maintenance of strength required for the photodetecting unit, by means of determining the thickness of the reinforcing member 49 as needed.

By means of the configuration in which X radiation enters the scintillator 10 by way of the photodetecting unit 50, enhancement of image quality can be promoted still further.

In the X-ray imaging cassette 100, the photodetecting unit 50 of the main body 1 is bonded to the back side of the top plate 60A of the cassette. Therefore, the distance between the subject put on the top plate 60A and the photodetecting unit 50 becomes shorter, which leads to enhancement of sensitivity and improvements in MTF. Further, the photodetecting unit 50 is made slim as a result of removal of the substrate 51, whereby enhancement of picture quality can be made much further. In other words, the effect resultant from removal of the substrate 51 and provision of the reinforcing member 49 becomes more noteworthy by means of the configuration in which the scintillator 10 is exposed to X radiation applied from the direction of the photodetecting unit 50 and in which the photodetecting unit 50 is bonded to the top plate 60A.

Although a pattern of the main body 1 accommodated in the cassette housing 60 has been provided in the above descriptions, accommodating the main body 1 in the housing 60 is not indispensable. A working effect similar to that yielded by the X-ray imaging cassette 100 can be yielded by a configuration including the main body 1 and the support member for supporting the subject.

6. Example Modification

The configuration of the reinforcing member belonging to the photodetecting unit is not limited to that mentioned above.

As shown in FIG. 12, the reinforcing member can include; for instance, a base substance 49A (a resin layer) made of a resin and a light reflection film 49B (a light reflection layer) that is made of aluminum, or the like, and that is stacked on an X-ray entrance side of the base substance 49A.

Figure 13:
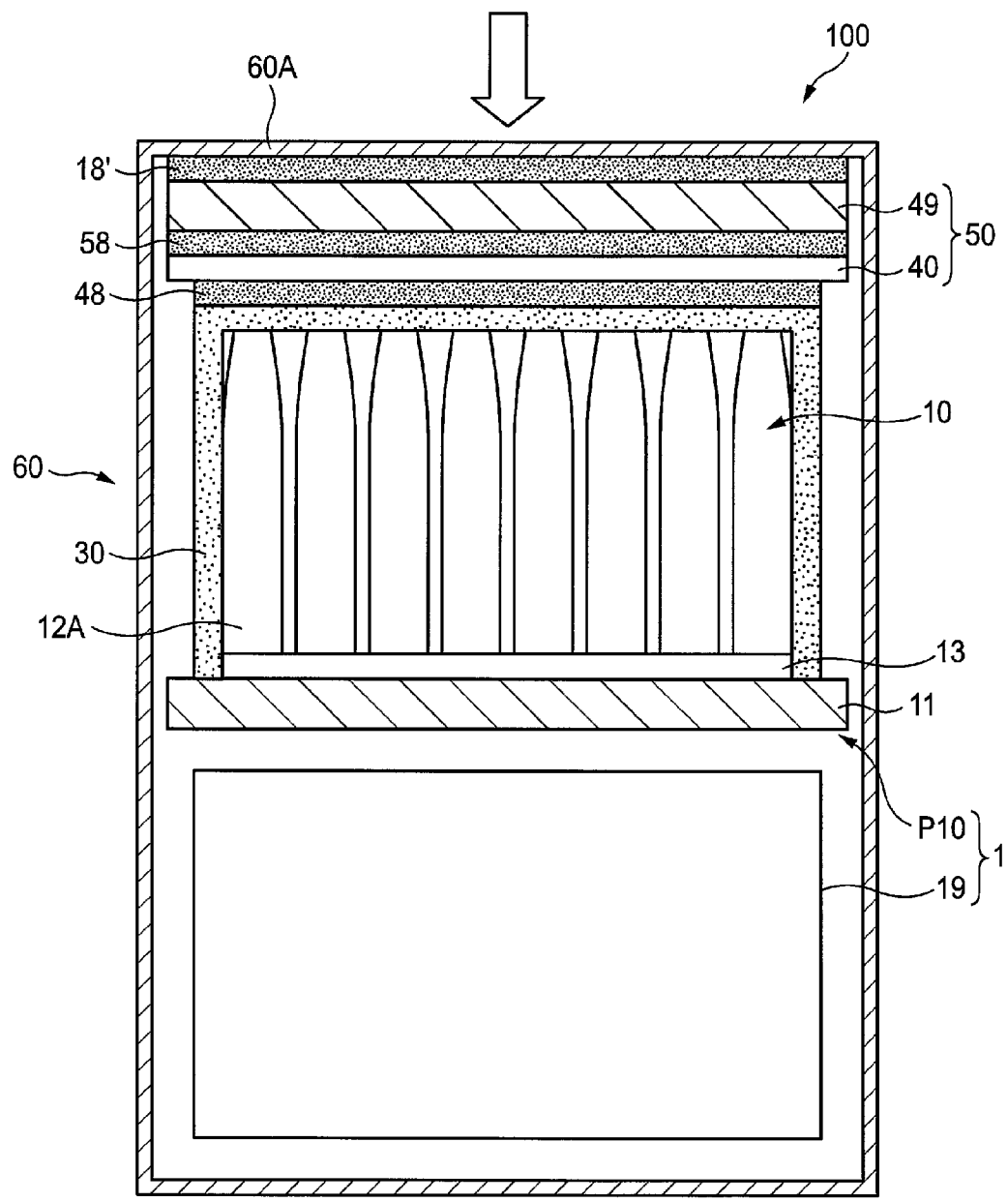
FIG. 13 is a side cross sectional view showing a state in which a top plate and the reinforcing member are bonded substantially in their entirety.

In the above descriptions, the joint area between the reinforcing member 49 and the top plate 60A is made smaller in consideration of ease of rework, whereby the bonding strength exerted between the reinforcing member 49 and the top plate 60A is reduced. However, the reinforcing member is not limited to this configuration. An adhesive whose bonding strength is lower than the bonding strength of the adhesive used for bonding the reinforcing member 49 to the thin film portion 40 is used as an adhesive used for bonding the reinforcing member 49 to the top plate 60A. Even in this case, the bonding strength exerted between the reinforcing member 49 and the top plate 60A can be made smaller than the bonding strength exerted between the reinforcing member 49 and the thin film portion 40. In this case, as shown in FIG. 13, the reinforcing member 49 and the top plate 60A can also be bonded together substantially in their entirety while there is sandwiched therebetween an adhesive layer 18' applied with a second adhesive whose bonding strength is smaller than the bonding strength of a first adhesive used for bonding the reinforcing member 49 to the thin film portion 40.

Figure 14:
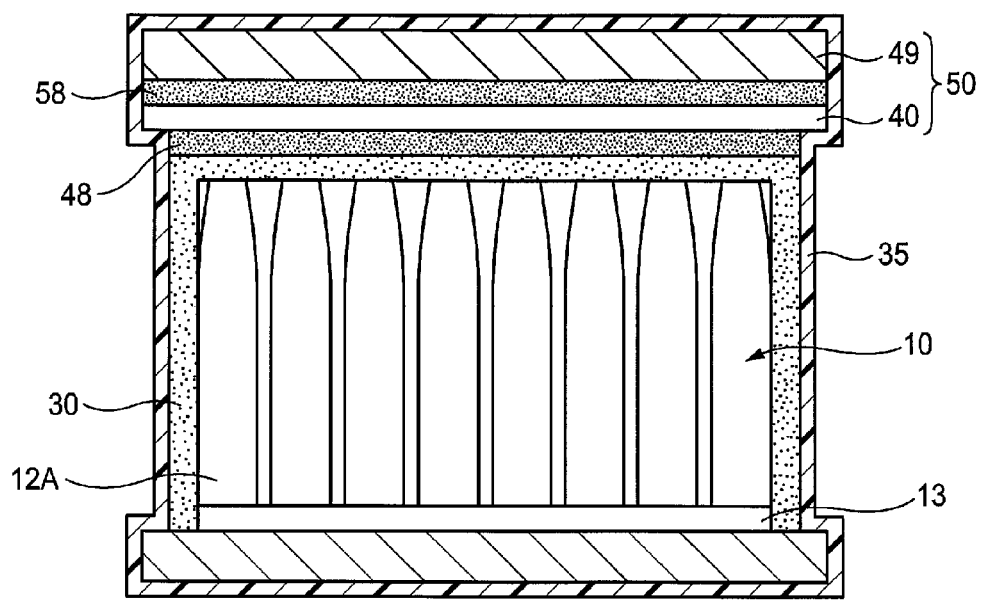
FIG. 14 is a side cross sectional view showing an example modification of a protective film.

FIG. 14 shows an example modification of the X-ray image detection apparatus. In the example modification, a protective film 35 that protects all of the support 11, the scintillator 10, and the photodetecting unit 50 is formed after peeling and removal of the substrate 51. In addition to the protective film 30 provided on the scintillator 10, the protective film 35 is also provided, whereby the scintillator 10 and the thin film portion 40 are definitely sealed. Therefore, deterioration of performance of the scintillator 10 and the thin film portion 40 can be sufficiently prevented. The protective film 35 does not always need to cover all of the support 11, the scintillator 10, and the photodetecting unit 50, as illustrated in FIG. 14. The protective film 35 may also be provided so as to cover side surfaces of each of the thin film portion 40 and the reinforcing member 49 and the surface of the reinforcing member 49 from which the substrate 51 has been peeled off.

Figure 15:
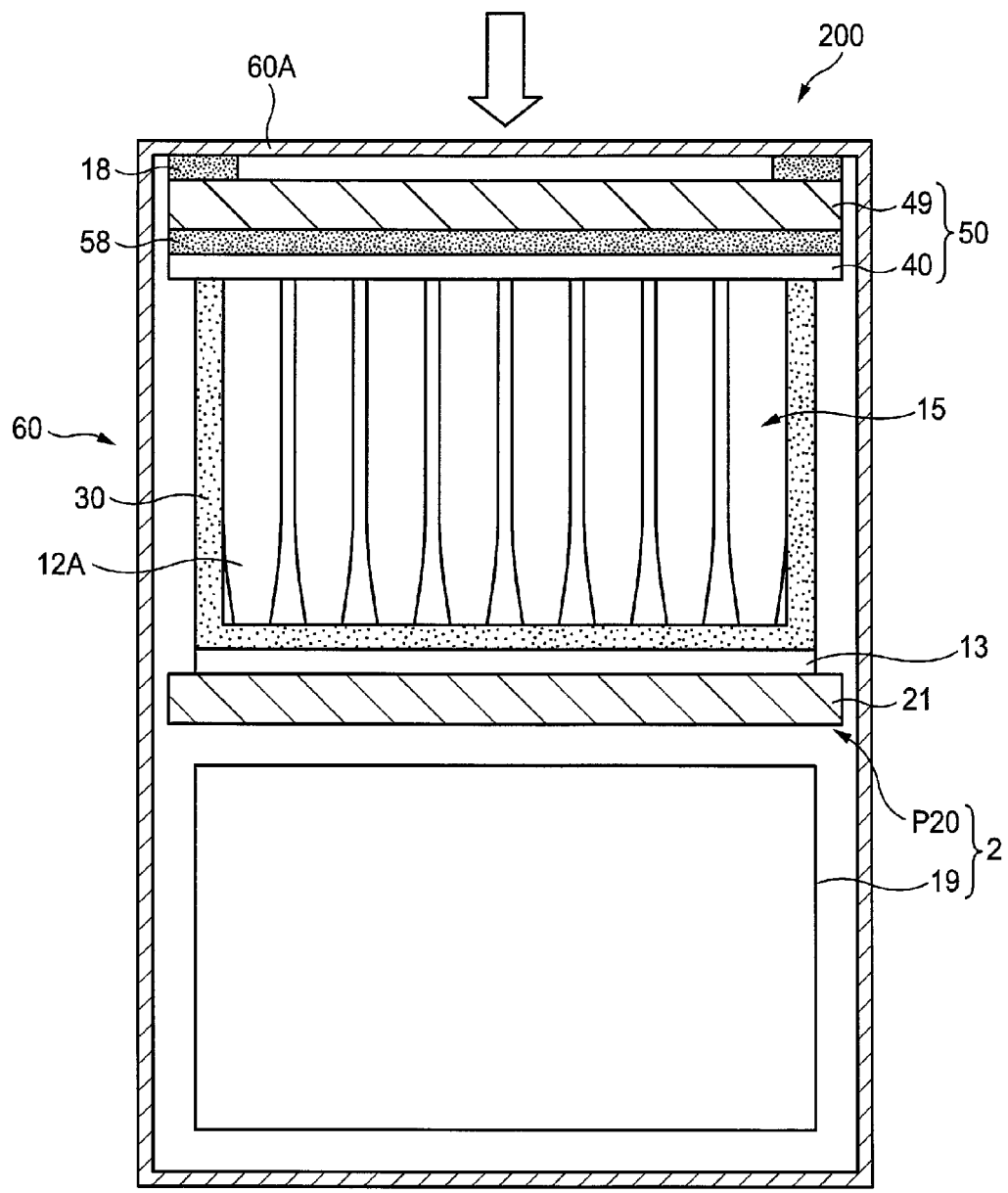
FIG. 15 is a side cross sectional view schematically showing a general configuration of an X-ray imaging cassette differing from that shown in FIG. 1.

FIG. 15 shows an X-ray imaging cassette 200. The X-ray imaging cassette 200 has an X-ray image detection apparatus main body 2 and the housing 60. In the X-ray image detection apparatus main body 1 shown in FIG. 1, the scintillator 10 and the photodetecting unit 50 are bonded together while the adhesive layer 48 is sandwiched therebetween. On the contrary, in the X-ray image detection apparatus main body 2 shown in FIG. 15, a scintillator 15 is deposited on the photodetecting unit 50. Besides this, the X-ray image detection apparatus main body 2 is configured similarly to the X-ray image detection apparatus main body 1.

On the occasion of manufacture of the X-ray imaging cassette 200, the thin film portion 40 is formed over the substrate 51 as shown in FIG. 7, and the scintillator 15 is deposited directly on the thin film portion 40. The scintillator 15 is then sealed with the protective film 30. The scintillator 15 is deposited on the thin film portion 40, whereby the scintillator 15 and the photodetecting unit 50 are integrated into one. Next, on the occasion of removal of the substrate 51, a support member 21 is placed on the other side of the scintillator 15 with respect to its side facing the thin film portion 40, thereby supporting the scintillator 15. Subsequently, the substrate 51 is peeled off from the thin film portion 40. It is desirable that the support member 21 be a light reflection member, like aluminum.

An X-ray image detection panel P20 not having the substrate 51 is thus manufactured. The scintillator 15 is deposited before removal of the substrate 51 as mentioned above, and the support member 21 is further provided. Thus, ease of handling of the thin film portion 40 can be enhanced, and damage on the columnar crystals 12A, which would otherwise be caused when the columnar crystals 12A contact each other during removal of the substrate, can be prevented. The X-ray image detection panel P20 manufactured as mentioned above is accommodated into the housing 60 in the same manner as in the case of the X-ray image detection panel P10, whereby the X-ray imaging cassette 200 is manufactured.

The scintillators 10 and 15 of the X-ray image detection apparatus main bodies 1 and 2 may not be provided with the non-columnar portion 13 including the non-columnar crystals 13A, such as those mentioned above. However, if the non-columnar portion 13 is formed, the following effect will be yielded. Namely, the non-columnar portion can be formed at an arbitrary position on the scintillator along the direction of crystal growth.

When a non-columnar portion is formed at a base end or leading end of the scintillator along its direction of crystal growth, it is possible to assure adhesion between a support and a photodetecting unit that will be integrated with the scintillator after formation of the scintillator or adhesion between the support on which the scintillator is deposited and the thin film portion. Assuring adhesion makes it possible to prevent removal of the scintillator from the support and the photodetecting unit and also deterioration of performance of the scintillator, which would otherwise be caused by absorption of moisture. Further, when a non-columnar portion is formed at the leading end of the columnar crystals, the surface of the scintillator is planarized by means of the non-columnar portion. Accordingly, the scintillator and the photodetecting unit can uniformly be bonded together. Quality of a detected image can thereby be enhanced. When the non-columnar portion is formed at the base end (i.e., an initially deposited area) of the scintillator, the columnar crystals can be caused to grow with superior crystalline on the basis of the non-columnar portion.

The strength of the scintillator can be enhanced by means of providing the columnar portion with the non-columnar portion. Impact resistance of the scintillator can thereby be enhanced. Further, it is possible to assure strength against load which will be imposed on the scintillator when the scintillator and the support or the photodetecting unit are bonded together. Hence, the scintillator and the photodetecting unit, or the like, can be firmly pressed against each other and uniformly brought into close contact with each other. Moreover, it is possible to increase withstand load of a cassette formed by bonding the panel, which is formed by inclusion of the scintillator, to the top plate of the housing as a result of enhancement of strength of the scintillator. On this occasion, since the substrate has already been peeled off from the photodetecting unit, the top plate and the respective photodetecting units come further closer to each other. Hence, an effect of enhancing sensitivity and image quality can be further increased. As a result of the non-columnar portion being formed at the leading end of the columnar portion, inflow of a material of the protective film into gaps among the columnar crystals can be prevented. Hence, an effect of preventing deterioration of MTF is also yielded.

Figure 16:
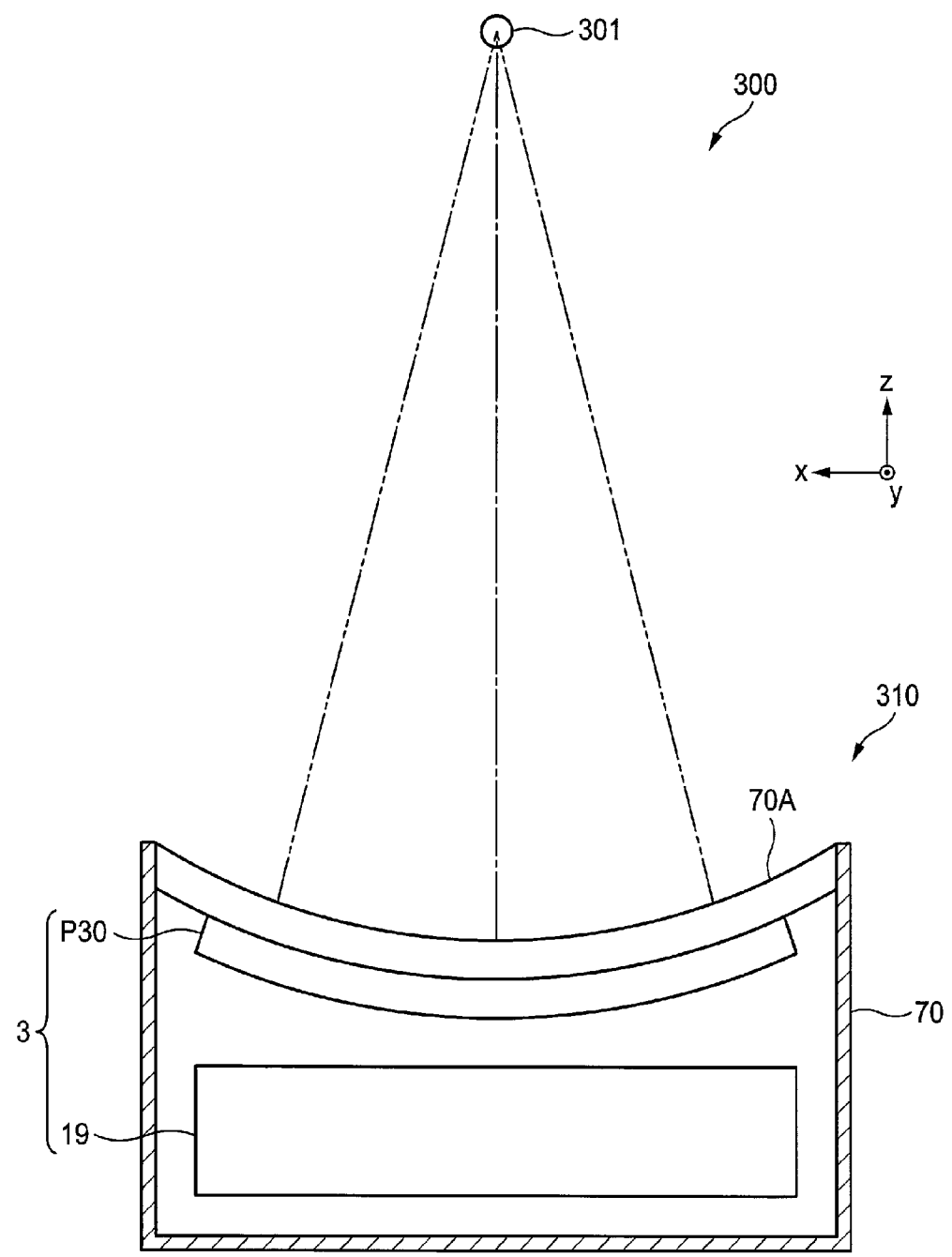
FIG. 16 is a schematic view showing a general configuration of an X-ray imaging system equipped with a concavely curved X-ray image detection panel.
Figure 17:
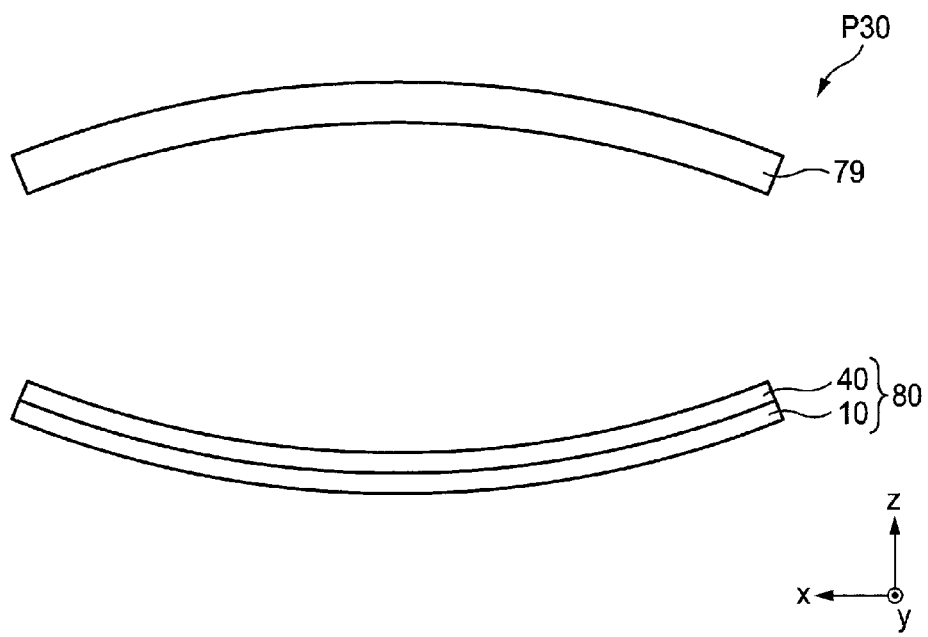
FIG. 17 is a schematic view showing a convexly curved reinforcing member and a concavely curved scintillator panel.
Figure 18:
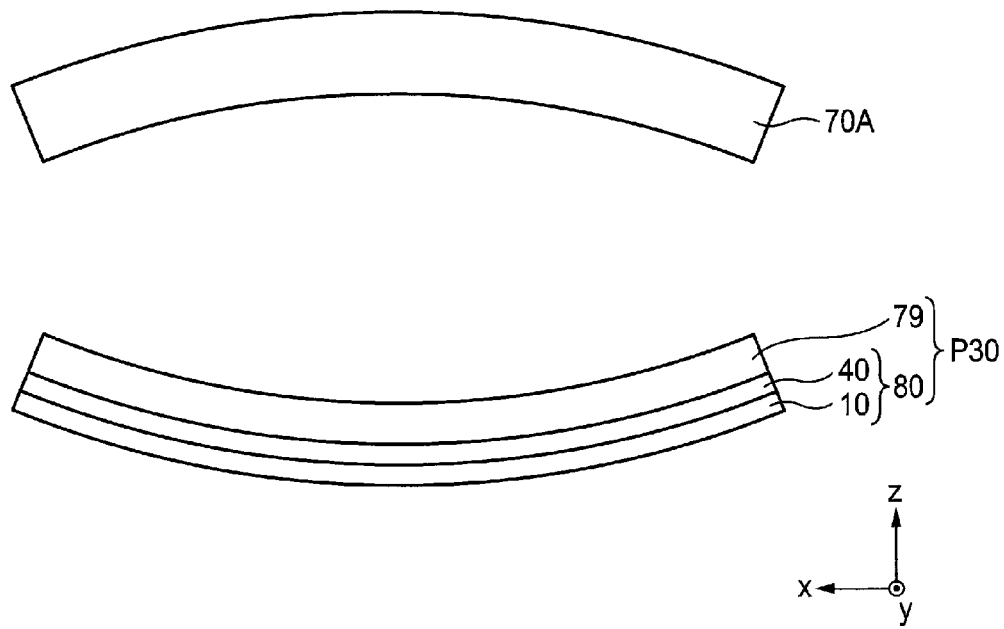
FIG. 18 is a schematic diagram showing a convexly-curved top plate and a concavely curved X-ray image detection panel.

FIGS. 16 to 18 schematically show a general configuration of an X-ray imaging system 300 having an X-ray imaging cassette 310 that differs from its counterparts described above. The X-ray imaging system 300 includes an X-ray source 301 serving as a radiation source and the X-ray imaging cassette 310 exposed to X radiation emitted from the X-ray source 301 by way of an unillustrated collimator, or the like. The X-ray imaging cassette 310 is equipped with a housing 70 including a top plate 70A and a main body 3 serving as a radiological image detection apparatus main body accommodated in the housing 70. Curved shapes of the respective members shown in FIGS. 16 to 18 are illustrated in such a way that curvatures of the respective members are greatly exaggerated.

Although simplified in FIG. 16, the main body 3 has an X-ray image detection panel P30 that is an integration of a scintillator, a thin film portion, and a reinforcing member. While accommodated in the housing 70 as shown in FIG. 16, the X-ray image detection panel P30 is convexly curved toward the control module 19. Put otherwise, the X-ray image detection panel P30 is curved so as to become concavely indented from the X-ray entrance side toward the control module 19. In subsequent descriptions, in relation to the orientation of the curve of the member, when the member is curved toward the X-ray entrance side in a projecting manner, the member is referred to as being convexly curved. On the contrary, when the member is curved in a direction opposite to the X-ray entrance side in a projecting manner, the curve is referred to as being concavely curved. Specifically, the X-ray image detection panel P30 is concavely curved.

FIG. 17 is an exploded schematic view of the X-ray image detection panel P30. The X-ray image detection panel P30 has a reinforcing member 79 convexly curved toward the X-ray entrance side and a concavely curved scintillator panel 80. After the thin film portion 40 from which the substrate 51 has been peeled off as shown in FIG. 9 and the scintillator 10 have been integrated into one, the scintillator panel 80 is concavely curved. Since the substrate 51 is peeled off from the photodetecting unit 50, it is easy to curve, as mentioned above, a laminate consisting of the thin film portion 40 and the scintillator 10. The thus concavely curved scintillator panel 80 and the convex reinforcing member 79 are bonded together while an unillustrated adhesive layer is sandwiched therebetween. The scintillator panel 80 and the reinforcing member 79 are pressed against each other along a laminate plane therebetween, to thus be integrated into one while remaining in a closely, uniformly contact with each other. The X-ray image detection panel P30 is thereby formed.

Repulsive force developing when the curved reinforcing member 79 is pressed against the scintillator panel 80 contributes to an increase in strength of the laminate consisting of the reinforcing member 79 and the scintillator panel 80. Thus, there is acquired strength that is greater than strength determined by a material and a dimension, like a thickness, of the reinforcing member 79 and the scintillator panel 80, or the like. The reinforcing member 79 is convexly curved, and also the scintillator panel 80 is concavely curved. Thus, repulsive force that develops when the members curved in different orientations are bonded together produces strength, whereby the strength of the laminate into which the members are stacked can be enhanced to a much greater extent.

Since the strength can be increased as mentioned above, the deflection of the scintillator panel 80 caused by the weight of the scintillator 10 can be prevented even when the thickness of the reinforcing member 79 is reduced. Specifically, the reinforcing member 79 is convexly curved, whereby absorption of X radiation occurred on the X-ray entrance side of the scintillator 10 can be reduced much greater, so that image quality can be enhanced. Moreover, since the thickness of the reinforcing member 79 is small, the distance between the subject and the thin film portion 40 can be shortened, whereby detection sensitivity and MTF can be enhanced.

The shape of the X-ray image detection panel P30 formed as a result of the convex reinforcing member 79 and the concave scintillator panel 80 being bonded together may be a substantial flat shape or a curve, such as that shown in FIG. 18. Although the thin film portion 40 shown in FIG. 17 is concavely curved, the thin film portion 40 may also assume a substantially flat shape. The curved shape (a degree of deflection) of the X-ray image detection panel P30 can be controlled by the convex shape of the reinforcing member 79.

FIG. 18 is a schematic diagram of the concavely curved X-ray image detection panel P30 and the top plate 70A convexly curved toward the X-ray entrance side. The top plate 70A and the X-ray image detection panel P30 are pressed against each other, whereby repulsive force of the top plate 70A and repulsive force of the X-ray image detection panel P30 contribute to an increase in strength. Therefore, the thickness of the reinforcing member 79 can be reduced, and withstand load of the top plate 70A and the X-ray image detection panel P30 can be increased. The thin film portion 40 can be sufficiently reinforced even by means of the thin reinforcing member 79. In relation to bonding of the top plate 70A to the reinforcing member 79, an adhesion area and adhesion force of an adhesive are determined in consideration of ease of rework in such a way that the minimum required adhesive force can be assured.

Although the X-ray image detection panel P30 can be given a flat shape, it is desirable that the X-ray image detection panel P30 be formed into a concave shape in order to enhance strength and that the X-ray image detection panel P30 be bonded to the convex top plate 70A.

The laminate formed as a result of the convex top plate 70A being bonded to the concave X-ray image detection panel P30 may be given a substantially flat shape or a curve, such as that shown in FIG. 16. When the laminate is curved as shown in FIG. 16, a conical cone beam emitted from the X-ray source 301 by way of the collimator (not shown) can be caused to enter, in a collimated fashion, the columnar crystals 12A (FIG. 4) of the scintillator 10. Accordingly, crosstalk among the pixels can be lessened, so that image quality can be enhanced.

Moreover, since the X-ray image detection panel P30 is concavely curved, there is also yielded an advantage of the surface of the top plate 70A being less susceptible to flaws when a plurality of cassettes are conveyed while being piled.

Despises these points, the X-ray imaging cassette 310 is configured in a similar fashion as is the X-ray imaging cassette 100 or the X-ray imaging cassette 200. Further, a working effect similar to those mentioned above is also yielded.

the reinforcing member 79, the scintillator panel 80, the top plate 70A, and the X-ray image detection panel P30 are curved in a direction X from one end of a traveling direction of X radiation (i.e., a direction "z") to the other side as illustrated in FIGS. 16 to 18 and are not curved in a direction "y" (a direction perpendicular to a drawing sheet). Specifically, the reinforcing member 79, the scintillator panel 80, the top plate 70A, and the X-ray image detection panel P30 are respectively formed into a channel member having a substantially C-shaped cross sectional profile.

Various schemes are available for the X-ray imaging device to acquire an image. However, when an image is formed by scanning strength of and a phase difference in X radiation passed through a subject in the direction "x" in FIGS. 16 to 18, the essential requirement for the X-ray image detection panel P30 is to be curved in only the direction "x" in which crosstalk poses a problem. When a scan is performed in both directions "x" and "y," the respective members of the reinforcing member 79 may also be curved in both "x" and "y" directions.

Figure 19:
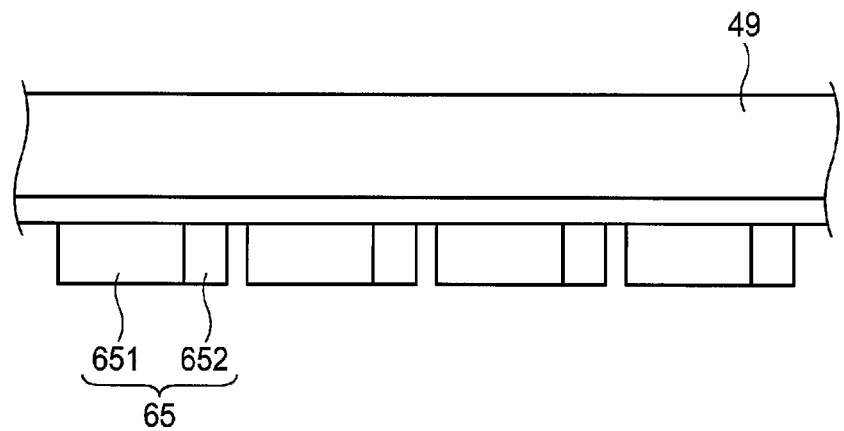
FIG. 19 is a schematic view showing an example modification of the thin film portion of the photodetecting unit.

FIG. 19 shows another thin film portion 65 that can be replaced with the thin film portion 40 shown in FIG. 2. PDs 651 and TFTs 652 belonging to the thin film portion 65 are arranged within the same plane or the substantially same plane. As a result of the PDs 651 and the TFTs 652 being arranged side by side within a plane as mentioned above, the thin film portion 65 can be made much thinner.

A TFT fabricated of an amorphous oxide semiconductor (a-IGZO) can be used for both the thin film portion 40 shown in FIG. 2 and the thin film portion 65 shown in FIG. 19. Sensitivity of a-IGZO is a wavelength of 350 nm or more, and sensitivity is hardly achieved in a visible light range. Therefore, switching noise does not occur in the TFTs. A necessity for providing the TFTs with a light reflection layer can be obviated.

Figure 20:
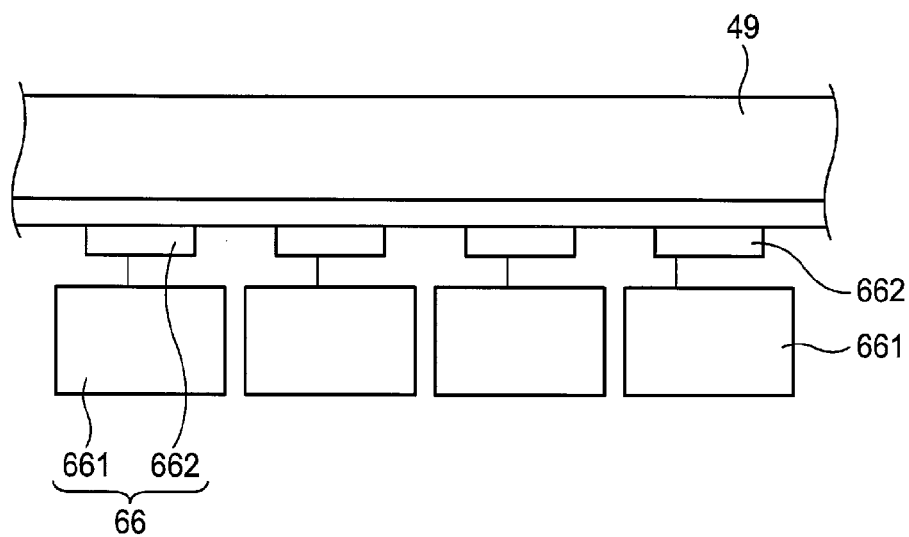
FIG. 20 is a schematic view showing another example modification of the thin film portion of the photodetecting unit.

An organic material can also be used for the PDs and the TFTs. FIG. 20 shows photoelectric conversion elements 661 having a photoconductive layer formed from an OPC (organic photoelectric conversion material) and TFTs 662 formed from an organic material. A thin film portion 66 including the photoelectric conversion elements 661 and the TFTs 662 can also be replaced with the thin film portion 40 shown in FIG. 2.

The organic material used for the photoelectric conversion elements 661 and the TFTs 662 hardly absorbs X radiation. Hence, the quantity of X radiation that reach the scintillator 10 after having passed through the photoelectric conversion elements 661 and the TFTs 662 can be increased. When CsI:Tl that emits green light is used for the scintillator and when the transparent organic material of the TFTs is a phthalocyanine compound expressed by the chemical formula 1 descried in; for instance, JP-A-2009-212389 or a naphthalocyanine compound expressed by the chemical formula 2 descried in the same, sensitivity is not exhibited in a luminous wavelength range. Therefore, switching noise does not occur in the TFTs. In this case, the OPC of the photoelectric conversion elements 661 is preferably quinacridone.

The photoelectric conversion elements 661 and the TFTs 662 formed from the organic material may also be placed on the same plane or substantially the same plane, as shown in FIG. 19.

The photoelectric conversion element, like a PD, and the TFTs formed from an amorphous oxide or an organic material, such as those mentioned above, can be caused to grow at a temperature that is lower than the temperature used for forming a-Si. Therefore, a room for choice of a material of the reinforcing member 49 becomes broader, and a reinforcing member made of a resin also becomes usable. As a matter of course, the convex reinforcing member 79 can also be provided on the thin film portions 65 and 66 shown in FIGS. 19 and 20.

7. Available Device Material

[7-1. OPC (Organic Photoelectric Conversion) Material]

For example, any OPC (Organic Photoelectric Conversion) material disclosed in JP-A-2009-32854 can be used for the aforementioned PDs 41 (FIG. 2) or the like. A film formed out of the OPC material (hereinafter referred to as OPC film) can be used as the photoconductive layer of the PDs 41. The OPC film contains an organic photoelectric conversion material, which absorbs light emitted from the scintillator and generates electric charges corresponding to the absorbed light. Thus, the OPC film containing the organic photoelectric conversion material has a sharp absorption spectrum in a visible light range. Electromagnetic waves other than the light emitted by the scintillator are hardly absorbed by the OPC film. Thus, noise generated by radioactive rays such as X-rays absorbed by the OPC film can be suppressed effectively.

It is preferable that the absorption peak wavelength of the organic photoelectric conversion material forming the OPC film is closer to the peak wavelength of light emitted by the scintillator in order to more efficiently absorb the light emitted by the scintillator. Ideally, the absorption peak wavelength of the organic photoelectric conversion material agrees with the peak wavelength of the light emitted by the scintillator. However, if the difference between the absorption peak wavelength of the organic photoelectric conversion material and the peak wavelength of the light emitted by the scintillator is small, the light emitted by the scintillator can be absorbed satisfactorily. Specifically, the difference between the absorption peak wavelength of the organic photoelectric conversion material and the peak wavelength of the light emitted by the scintillator in response to radioactive rays is preferably not larger than 10 nm, more preferably not larger than 5 nm.

Examples of the organic photoelectric conversion material that can satisfy such conditions include arylidene-based organic compounds, quinacridone-based organic compounds, and phthalocyanine-based organic compounds. For example, the absorption peak wavelength of quinacridone in a visible light range is 560 nm. Therefore, when quinacridone is used as the organic photoelectric conversion material and CsI(Tl) is used as the fluorescent material of the scintillator, the aforementioned difference in peak wavelength can be set within 5 nm so that the amount of electric charges generated in the OPC film can be increased substantially to the maximum.

At least a part of an organic layer provided between the bias electrode and the charge collection electrode of PD 41 can be formed out of an OPC film. More specifically, the organic layer can be formed out of a stack or a mixture of a portion for absorbing electromagnetic waves, a photoelectric conversion portion, an electron transport portion, an electron hole transport portion, an electron blocking portion, an electron hole blocking portion, a crystallization prevention portion, electrodes, interlayer contact improvement portions, etc.

Preferably the organic layer contains an organic p-type compound or an organic n-type compound. An organic p-type semiconductor (compound) is a donor-type organic semiconductor (compound) as chiefly represented by an electron hole transport organic compound, meaning an organic compound having characteristic to easily donate electrons. More in detail, of two organic materials used in contact with each other, one with lower ionization potential is called the donor-type organic compound. Therefore, any organic compound may be used as the donor-type organic compound as long as the organic compound having characteristic to donate electrons. Examples of the donor-type organic compound that can be used include a triarylamine compound, a benzidine compound, a pyrazoline compound, a styrylamine compound, a hydrazone compound, a triphenylmethane compound, a carbazole compound, a polysilane compound, a thiophene compound, a phthalocyanine compound, a cyanine compound, a merocyanine compound, an oxonol compound, a polyamine compound, an indole compound, a pyrrole compound, a pyrazole compound, a polyarylene compound, a fused aromatic carbocyclic compound (naphthalene derivative, anthracene derivative, phenanthrene derivative, tetracene derivative, pyrene derivative, perylene derivative, fluoranthene derivative), a metal complex having a nitrogen-containing heterocyclic compound as a ligand, etc. The donor-type organic semiconductor is not limited thereto but any organic compound having lower ionization potential than the organic compound used as an n-type (acceptor-type) compound may be used as the donor-type organic semiconductor.

The n-type organic semiconductor (compound) is an acceptor-type organic semiconductor (compound) as chiefly represented by an electron transport organic compound, meaning an organic compound having characteristic to easily accept electrons. More specifically, when two organic compounds are used in contact with each other, one of the two organic compounds with higher electron affinity is the acceptor-type organic compound. Therefore, any organic compound may be used as the acceptor-type organic compound as long as the organic compound having characteristic to accept electrons. Examples thereof include a fused aromatic carbocyclic compound (naphthalene derivative, anthracene derivative, phenanthrene derivative, tetracene derivative, pyrene derivative, perylene derivative, fluoranthene derivative), a 5- to 7-membered heterocyclic compound containing a nitrogen atom, an oxygen atom or a sulfur atom (e.g. pyridine, pyrazine, pyrimidine, pyridazine, triazine, quinoline, quinoxaline, quinazoline, phthalazine, cinnoline, isoquinoline, pteridine, acridine, phenazine, phenanthroline, tetrazole, pyrazole, imidazole, thiazole, oxazole, indazole, benzimidazole, benzotriazole, benzoxazole, benzothiazole, carbazole, purine, triazolopyridazine, triazolopyrimidine, tetrazaindene, oxadiazole, imidazopyridine, pyralidine, pyrrolopyridine, thiadiazolopyridine, dibenzazepine, tribenzazepine etc.), a polyarylene compound, a fluorene compound, a cyclopentadiene compound, a silyl compound, and a metal complex having a nitrogen-containing heterocyclic compound as a ligand. The acceptor-type organic semiconductor is not limited thereto. Any organic compound may be used as the acceptor-type organic semiconductor as long as the organic compound has higher electron affinity than the organic compound used as the donor-type organic compound.

As for p-type organic dye or n-type organic dye, any known dye may be used. Preferred examples thereof include cyanine dyes, styryl dyes, hemicyanine dyes, merocyanine dyes (including zero-methine merocyanine (simple merocyanine)), trinuclear merocyanine dyes, tetranuclear merocyanine dyes, rhodacyanine dyes, complex cyanine dyes, complex merocyanine dyes, alopolar dyes, oxonol dyes, hemioxonol dyes, squarylium dyes, croconium dyes, azamethine dyes, coumarin dyes, arylidene dyes, anthraquinone dyes, triphenylmethane dyes, azo dyes, azomethine dyes, spiro compounds, metallocene dyes, fluorenone dyes, flugide dyes, perylene dyes, phenazine dyes, phenothiazine dyes, quinone dyes, indigo dyes, diphenylmethane dyes, polyene dyes, acridine dyes, acridinone dyes, diphenylamine dyes, quinacridone dyes, quinophthalone dyes, phenoxazine dyes, phthaloperylene dyes, porphyrin dyes, chlorophyll dyes, phthalocyanine dyes, metal complex dyes, and fused aromatic carbocyclic dyes (naphthalene derivative, anthracene derivative, phenanthrene derivative, tetracene derivative, pyrene derivative, perylene derivative, fluoranthene derivative).

A photoelectric conversion film (photosensitive layer) which has a layer of a p-type semiconductor and a layer of an n-type semiconductor between a pair of electrodes and at least one of the p-type semiconductor and the n-type semiconductor is an organic semiconductor and in which a bulk heterojunction structure layer including the p-type semiconductor and the n-type semiconductor is provided as an intermediate layer between those semiconductor layers may be used preferably. The bulk heterojunction structure layer included in the photoelectric conversion film can cover the defect that the carrier diffusion length of the organic layer is short. Thus, the photoelectric conversion efficiency can be improved. The bulk heterojunction structure has been described in detail in JP-A-2005-303266.

It is preferable that the photoelectric conversion film is thicker in view of absorption of light from the scintillator. The photoelectric conversion film is preferably not thinner than 30 nm and not thicker than 300 nm, more preferably not thinner than 50 nm and not thicker than 250 nm, particularly more preferably not thinner than 80 nm and not thicker than 200 nm in consideration of the ratio which does make any contribution to separation of electric charges.

As for any other configuration about the aforementioned OPC film, for example, refer to description in JP-A-2009-32854.

[7-2. Organic TFT (Thin Film Transistor)]

Although inorganic materials are often used for the aforementioned TFTs 42 or the like, organic materials may be used, for example, as disclosed in JP-A-2009-212389. Organic TFT may have any type of structure but a field effect transistor (FET) structure is the most preferable. In the FET structure, a substrate is disposed in the bottom layer, and a gate electrode is provided partially an upper surface of the substrate. An insulator layer is provided to cover the electrode and touch the substrate in the other portion than the electrode. Further, a semiconductor active layer is provided on an upper surface of the insulator layer, and a source electrode and a drain electrode are disposed partially on the upper surface of the semiconductor active layer and at a distance from each other. This configuration is called a top contact type device. A bottom contact type device in which a source electrode and a drain electrode are disposed under a semiconductor active layer may be also used preferably. In addition, a vertical transistor structure in which a carrier flows in the thickness direction of an organic semiconductor film may be used.

(Semiconductor Active Layer)

A p-type organic semiconductor material is used as the material of the semiconductor active layer. The p-type organic semiconductor material is substantially colorless and transparent. For example, the thickness of the organic semiconductor thin film may be measured by a stylus thickness meter. A plurality of thin films with different thicknesses may be manufactured and their absorption spectra may be measured so that the maximum absorbance per film thickness of 30 nm can be obtained by conversion based on a calibration curve.

Organic semiconductor materials mentioned herein are organic materials showing properties as semiconductors. Examples of the organic semiconductor materials include p-type organic semiconductor materials (or referred to as p-type materials simply or as electron hole transport materials) which conduct electron holes (holes) as carriers, and n-type organic semiconductor materials (or referred to as n-type materials simply or as electrode transport materials) which conduct electrons as carriers, similarly to a semiconductor formed out of an inorganic material. Of the organic semiconductor materials, lots of p-type materials generally show good properties. In addition, p-type transistors are generally excellent in operating stability as transistors under the atmosphere. Here, description here will be made on a p-type organic semiconductor material.

One of properties of organic thin film transistors is a carrier mobility (also referred to as mobility simply) μ which indicates the mobility of a carrier in an organic semiconductor layer. Although preferred mobility varies in accordance with applications, higher mobility is generally preferred. The mobility is preferably not lower than $1.0*10^{-7}$ cm$^2$/Vs, more preferably not lower than $1.0*10^{-6}$ cm$^2$/Vs, further preferably not lower than $1.0*10^{-5}$ cm$^2$/Vs. The mobility can be obtained by properties or TOF (Time Of Flight) measurement when the field effect transistor (FET) device is manufactured.

The p-type organic semiconductor material may be either a low molecular weight material or a high molecular weight material, but preferably a low molecular weight material. Lots of low molecular weight materials typically show excellent properties due to easiness in high purification because various refining processes such as sublimation refining, recrystallization, column chromatography, etc. can be applied thereto, or due to easiness in formation of a highly ordered crystal structure because the low molecular weight materials have a fixed molecular structure. The molecular weight of the low molecular weight material is preferably not lower than 100 and not higher than 5,000, more preferably not lower than 150 and not higher than 3,000, further more preferably not lower than 200 and not higher than 2,000.

Preferred specific examples of such a p-type organic semiconductor material will be shown. Bu represents a butyl group, Pr represents a propyl group, Et represents an ethyl group, and Ph represents a phenyl group.

[Chemical 1]

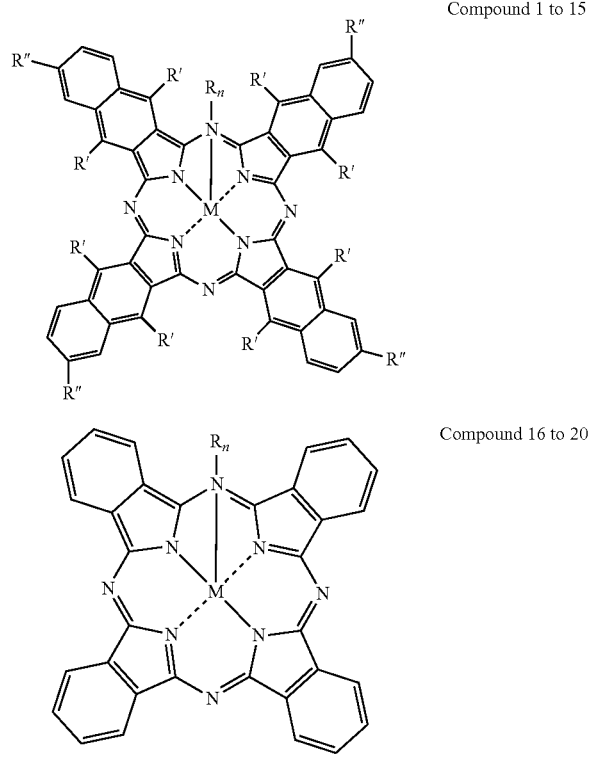

Compound 1 to 15

Compound 16 to 20

| Compound | M | R | n | R' | R" |
|---|---|---|---|---|---|
| 1 | Si | OSi(n-Bu)$_3$ | 2 | H | H |
| 2 | Si | OSi(i-Pr)$_3$ | 2 | H | H |
| 3 | Si | OSi(OEt)$_3$ | 2 | H | H |
| 4 | Si | OSiPh$_3$ | 2 | H | H |
| 5 | Si | O(n-C$_8$H$_{17}$) | 2 | H | H |
| 7 | Ge | OSi(n-Bu)$_3$ | 2 | H | H |
| 8 | Sn | OSi(n-Bu)$_3$ | 2 | H | H |
| 9 | Al | OSi(n-C$_6$H$_{13}$)$_3$ | 1 | H | H |
| 10 | Ga | OSi(n-C$_6$H$_{13}$)$_3$ | 1 | H | H |
| 11 | Cu | — | — | O(n-Bu) | H |
| 12 | Ni | — | — | O(n-Bu) | H |
| 13 | Zn | — | — | H | t-Bu |
| 14 | V=O | — | — | H | t-Bu |
| 15 | H$_2$ | — | — | H | t-Bu |
| 16 | Si | OSiEt$_3$ | 2 | — | — |
| 17 | Ge | OSiEt$_3$ | 2 | — | — |
| 18 | Sn | OSiEt$_3$ | 2 | — | — |
| 19 | Al | OSiEt$_3$ | 1 | — | — |
| 20 | Ga | OSiEt$_3$ | 1 | — | — |

(Device Constituent Materials Other than Semiconductor Active Layer)

Description will be made below on device constituent materials other than the semiconductor active layer in the organic thin film transistor. The visible-light or infrared-light transmittance of each of those materials is preferably not lower than 60%, more preferably not lower than 70%, further more preferably not lower than 80%.

The substrate is not limited particularly as long as it has required smoothness. Examples of the substrate include glass, quartz, light transmissive plastic film, etc. Examples of the light transmissive plastic film include films or the like, made from polyethylene terephthalate (PET), polyethylene naphthalate (PEN), polyether sulfone (PES), polyether imide, polyetheretherketone, polyphenylene sulfide, polyalylate, polyimide, polycarbonate (PC), cellulose triacetate (TAC), cellulose acetate propionate (CAP), etc. In addition, any organic or inorganic filler may be contained in these plastic films. A flexible substrate formed out of aramid, bionanofiber, or the like may be used preferably as the substrate.

The material forming the gate electrode, the source electrode or the drain electrode is not limited especially if it has required electric conductivity. Examples thereof include electrically conductive oxides such as ITO (indium-doped tin oxide), IZO (indium-doped zinc oxide), SnO$_2$, ATO (antimony-doped tin oxide), ZnO, AZO (aluminum-doped zinc oxide), GZO (gallium-doped zinc oxide), TiO$_2$, FTO (fluorine-doped tin oxide), etc., electrically conductive polymers such as PEDOT/PSS (poly(3,4-ethylenedioxythiophene)/polystyrenesulfonate), carbon materials such as carbon nanotube, etc. These electrode materials may be formed into films, for example, by a method such as a vacuum deposition method, sputtering, a solution application method, etc.

The material used for the insulating layer is not limited particularly as long as it has required insulating effect. Examples thereof include inorganic materials such as silicon dioxide, silicon nitride, alumina, etc., and organic materials such as polyester, (PEN (polyethylene naphthalate), PET (polyethylene terephthalate) etc.), polycarbonate, polyimide, polyamide, polyacrylate, epoxy resin, polyparaxylylene resin, novolak resin, PVA (polyvinyl alcohol), PS (polystyrene), etc. These insulating film materials may be formed into films, for example, by a method such as a vacuum deposition method, sputtering, a solution application method, etc.

As for any other configuration about the aforementioned organic TFT, for example, refer to description in JP-A-2009-212389.

[7-3. Amorphous Oxide Semiconductor]

For example, amorphous oxide disclosed in JP-A-2010-186860 may be used for the aforementioned TFTs 42. Here, description will be made on an amorphous oxide containing active layer of a FET transistor disclosed in JP-A-2010-186860. The active layer serves as a channel layer of the FET transistor where electrons or holes move.

The active layer has a configuration containing an amorphous oxide semiconductor. The amorphous oxide semiconductor can be formed into a film at a low temperature. Thus, the amorphous oxide semiconductor is formed preferably on a flexible substrate.

The amorphous oxide semiconductor used for the active layer is preferably amorphous oxide containing at least one kind of element selected from a group consisting of In, Sn, Zn and Cd, more preferably amorphous oxide containing at least one kind of element selected from a group consisting of In, Sn and Zn, further preferably amorphous oxide containing at least one kind of element selected from a group consisting of In and Zn.

Specific examples of the amorphous oxide used for the active layer include $In_2O_3$, ZnO, $SnO_2$, CdO, Indium-Zinc-Oxide (IZO), Indium-Tin-Oxide (ITO), Gallium-Zinc-Oxide (GZO), Indium-Gallium-Oxide (IGO), and Indium-Gallium-Zinc-Oxide (IGZO).

It is preferable that a vapor phase film formation method targeting at a polycrystal sinter of the oxide semiconductor is used as a method for forming the active layer. Of vapor phase film formation methods, a sputtering method or a pulse laser deposition (PLD) method is preferred. Further, the sputtering method is preferred in view from mass productivity. For example, the active layer is formed by an RF magnetron sputtering deposition method with a controlled degree of vacuum and a controlled flow rate of oxygen.

The thus formed active layer is confirmed to be an amorphous film by a well-known X-ray diffraction method. The composition ratio of the active layer is obtained by an RBS (Rutherford Backscattering Spectrometry) method.

In addition, the electric conductivity of the active layer is preferably lower than $10^2$ $Scm^{-1}$ and not lower than $10^4$ $Scm^{-1}$, more preferably lower than $10^2$ $Scm^{-1}$ and not lower than $10^{-1}$ $Scm^{-1}$. Examples of the method for adjusting the electric conductivity of the active layer include a known adjusting method using oxygen defect, an adjusting method using a composition ratio, an adjusting method using impurities, and an adjusting method using an oxide semiconductor material.

As for any other configuration about the aforementioned amorphous oxide, for example, refer to description in JP-A-2010-186860.

[7-4. Flexible Material]

It may be considered that aramid, bionanofiber, etc. having properties such as flexibility, low thermal expansion and high strength, which cannot be obtained in existing glass or plastic, are used in a radiological image detection apparatus.

(1) Aramid

A film formed out of aramid which is a flexible material may be used as the insulating substrate 401 of the aforementioned support 11, the control module 19, or the like. An aramid material has high heat resistance showing a glass transition temperature of 315° C., high rigidity showing a Young's modulus of 10 GPa, and high dimensional stability showing a thermal expansion coefficient of −3 to 5 ppm/° C. Therefore, when a film made from aramid is used, it is possible to easily form a high-quality film for a semiconductor layer or a scintillator, as compared with the case where a general resin film is used. In addition, due to the high heat resistance of the aramid material, a transparent electrode material can be cured at a high temperature to have low resistance. Further, it is also possible to deal with automatic mounting with ICs, including a solder reflow step. Furthermore, since the aramid material has a thermal expansion coefficient close to that of ITO (indium tin oxide), a gas barrier film or a glass substrate, warp after manufacturing is small. In addition, cracking hardly occurs. Here, it is preferable to use a halogen-free (in conformity with the requirements of JPCA-ES01-2003) aramid material containing no halogens, in view of reduction of environmental load.

The aramid film may be laminated with a glass substrate or a PET substrate, or may be pasted onto a housing of a device.

High intermolecular cohesion (hydrogen bonding force) of aramid leads to low solubility to a solvent. When the problem of the low solubility is solved by molecular design, an aramid material easily formed into a colorless and transparent thin film can be used preferably. Due to molecular design for controlling the order of monomer units and the substituent species and position on an aromatic ring, easy formation with good solubility can be obtained with the molecular structure kept in a bar-like shape with high linearity leading to high rigidity or dimensional stability of the aramid material. Due to the molecular design, halogen-free can be also achieved.

In addition, an aramid material having an optimized characteristic in an in-plane direction of a film can be used preferably. Tensional conditions are controlled in each step of solution casting, vertical drawing and horizontal drawing in accordance with the strength of the aramid film which varies constantly during casting. Due to the control of the tensional conditions, the in-plane characteristic of the aramid film which has a bar-like molecular structure with high linearity leading to easy occurrence of anisotropic physicality can be balanced.

Specifically, in the solution casting step, the drying rate of the solvent is controlled to make the in-plane thickness-direction physicality isotropic and optimize the strength of the film including the solvent and the peel strength from a casting drum. In the vertical drawing step, the drawing conditions are controlled precisely in accordance with the film strength varying constantly during drawing and the residual amount of the solvent. In the horizontal drawing, the horizontal drawing conditions are controlled in accordance with a change in film strength varying due to heating and controlled to relax the residual stress of the film. By use of such an aramid material, the problem that the aramid film after casting may be curled.

In each of the contrivance for the easiness of casting and the contrivance for the balance of the film in-plane characteristic, the bar-like molecular structure with high linearity peculiar to aramid can be kept to keep the thermal expansion coefficient low. When the drawing conditions during film formation are changed, the thermal expansion coefficient can be reduced further.

(2) Bionanofiber

Components sufficiently small relative to the wavelength of light produce no scattering of the light. Accordingly, a flexible plastic material, or the like, reinforced by nanofibers may be used preferably in the insulating substrate, the circuit board of the control module 19, or the like. Of the nanofibers, a composite material (occasionally referred to as bionanofiber) of bacterial cellulose and transparent resin can be used preferably. The bacterial cellulose is produced by bacteria (*Acetobacter Xylinum*). The bacterial cellulose has a cellulose microfibril bundle width of 50 nm, which is about 1/10 as large as the wavelength of visible light. In addition, the bacterial cellulose is characterized by high strength, high elasticity and low thermal expansion.

When a bacterial cellulose substrate is impregnated with transparent resin such as acrylic resin or epoxy resin and hardened, transparent bionanofiber showing a light transmittance of about 90% in a wavelength of 500 nm while having a high fiber ratio of about 60 to 70% can be obtained. By the bionanofiber, a thermal expansion coefficient (about 3 to 7 ppm) as low as that of silicon crystal, strength (about 460 MPa) as high as that of steel, and high elasticity (about 30 GPa) can be obtained.

As for the configuration about the aforementioned bionanofiber, for example, refer to description in JP-A-2008-34556.

Any of the X-ray imaging cassettes (and the X-ray imaging cassettes) that have been described thus far can be used while built in various systems, including a medical X-ray imaging system. In particular, each of the X-ray imaging cassettes characterized by high sensitivity and high resolution can be preferably used for a mammography system that is required to detect a sharp image at a low radiation dose.

Moreover, in addition to being used as the medical X-ray imaging system, the X-ray imaging cassettes can also be used as; for instance, an industrial X-ray imaging system for non-destructive inspection. In addition, the X-ray imaging cassettes using X radiation have been described as the examples in connection with the embodiment. However, another detector for radiation other than X radiation (alpha radiation, beta radiation, gamma radiation, or the like, other than the electromagnetic waves) can also be constructed in substantially the same way as is the X-ray imaging cassette 100.

8. Disclosure of Specification

It is disclosed a radiological image detection apparatus including: a radiological image detection apparatus main body including a scintillator that converts into fluorescence radiation emitted by way of a subject and a photodetecting unit provided on a radiation entrance side of the scintillator; and a support disposed on a radiation entrance side of the radiological image detection apparatus main body to support the subject. The photodetecting unit includes a thin film portion that detects the fluorescence as an electric signal and a reinforcing member that is provided on another side of the thin film portion with respect to its side facing the scintillator. The reinforcing member and the support are bonded together and remain in close contact with each other along a joint plane therebetween.

In the radiological image detection apparatus, the reinforcing member and the thin film portion may be bonded together. Bonding strength exerted between the reinforcing member and the thin film portion may be greater than bonding strength exerted between the reinforcing member and the support.

In the radiological image detection apparatus, mutually opposing surfaces of the reinforcing member and the thin film portion may be bonded substantially in their entirety. A part of an opposing surface of the reinforcing member facing the support may be bonded to the support.

In the radiological image detection apparatus, the reinforcing member and the thin film portion may be bonded together by means of a first adhesive. The reinforcing member and the support may be bonded together by means of a second adhesive whose bonding force is smaller than bonding force of the first adhesive.

In the radiological image detection apparatus, the reinforcing member may be convexly curved toward the radiation entrance side. The reinforcing member, the thin film portion, and the scintillator may be flat or substantially flat while the reinforcing member and the thin film portion remain bonded together.

In the radiological image detection apparatus, the reinforcing member may be convexly curved toward the radiation entrance side. The reinforcing member, the thin film portion, and the scintillator may be curved in a direction opposite to a direction of curvature of the reinforcing member while the reinforcing member and the thin film portion remain bonded together.

In the radiological image detection apparatus, the thin film portion and the scintillator may be curved in a direction opposite to a direction of curvature of the reinforcing member. The curved thin film portion and the scintillator and the convexly curved reinforcing member may be bonded together.

In the radiological image detection apparatus, the reinforcing member, the thin film portion, and the scintillator may be curved in a direction opposite to a direction of curvature of the reinforcing member while the reinforcing member and the thin film portion remain bonded together. The support may be convexly curved toward the radiation entrance side. The reinforcing member, the thin film portion, and the scintillator may be bonded to the support.

In the radiological image detection apparatus, the reinforcing member may be formed from an X-ray absorbent material whose X-ray absorbency is lower than X-ray absorbency of a glass material. An aluminum equivalent of the reinforcing member with respect to X radiation emitted at a tube voltage of 60 kV may be under 1.8 mm.

In the radiological image detection apparatus, the aluminum equivalent with respect to the X radiation emitted at the tube voltage of 60 kV when the support and the reinforcing member are used may be under 1.8 mm.

In the radiological image detection apparatus, the low X-ray absorbent material may be metal (including a metal compound and an alloy) and/or a resin.

In the radiological image detection apparatus, the reinforcing member may include a resin layer and a light reflection layer made of metal provided on an X-ray entrance side of the resin layer.

In the radiological image detection apparatus, the reinforcing member may be a light reflection member that reflects fluorescence emitted from the scintillator toward the thin film portion.

In the radiological image detection apparatus, the reinforcing member and the thin film portion may be bonded together while an adhesive layer is sandwiched therebetween. A thickness of the adhesive layer may be 100 micrometers or less.

In the radiological image detection apparatus, at least a part of the thin film portion may be formed from an amorphous oxide or an organic material.

In the radiological image detection apparatus, the scintillator may include a columnar portion formed from a group of columnar crystals resultant from columnar growth of crystals of a fluorescent material.

In the radiological image detection apparatus, the reinforcing member may be provided on a surface of the thin film portion from which the substrate supporting the thin film portion has been peeled off.

It is disclosed a radiographic imaging cassette including the aforementioned radiological image detection apparatus. The radiological image detection apparatus main body is accommodated in a housing formed by inclusion of the support.

It is disclosed a radiographic imaging system including: a radiation source that emits radiation to a subject; a support; and the aforementioned radiological image detection apparatus.

It is disclosed a radiological image detection apparatus including: a scintillator that converts radiation emitted by way of a subject into fluorescence and a photodetecting unit provided on a radiation entrance side of the scintillator. The photodetecting unit has a thin film portion for detecting the fluorescence as an electric signal and a reinforcing member disposed on another side of the thin film portion with respect to its side facing the scintillator. The reinforcing member and a support for supporting the subject are bonded together and remain in close contact with each other along a joint plane therebetween.

What is claimed is:

1. A radiological image detection apparatus comprising:
a radiological image detection apparatus main body including a scintillator that converts into fluorescence radiation emitted by way of a subject and a photodetecting unit provided on a radiation entrance side of the scintillator; and
a support disposed on a radiation entrance side of the radiological image detection apparatus main body to support the subject, wherein:
the photodetecting unit includes a thin film portion that detects the fluorescence as an electric signal and a reinforcing member that is provided on another side of the thin film portion with respect to its side facing the scintillator;
the reinforcing member and the support are bonded together and remain in close contact with each other along a joint plane therebetween;
the reinforcing member and the thin film portion are bonded together; and
bonding strength exerted between the reinforcing member and the thin film portion is greater than bonding strength exerted between the reinforcing member and the support.

2. The radiological image detection apparatus according to claim 1, wherein:
mutually opposing surfaces of the reinforcing member and the thin film portion are bonded substantially in their entirety; and
a part of an opposing surface of the reinforcing member facing the support is bonded to the support.

3. The radiological image detection apparatus according to claim 1, wherein:
the reinforcing member and the thin film portion are bonded together by means of a first adhesive; and
the reinforcing member and the support are bonded together by means of a second adhesive whose bonding force is smaller than bonding force of the first adhesive.

4. The radiological image detection apparatus according to claim 1, wherein:
the reinforcing member is convexly curved toward the radiation entrance side; and
the reinforcing member, the thin film portion, and the scintillator are flat or substantially flat while the reinforcing member and the thin film portion remain bonded together.

5. The radiological image detection apparatus according to claim 1, wherein:
the reinforcing member is convexly curved toward the radiation entrance side; and
the reinforcing member, the thin film portion, and the scintillator are curved in a direction opposite to a direction of curvature of the reinforcing member while the reinforcing member and the thin film portion remain bonded together.

6. The radiological image detection apparatus according to claim 4, wherein:
the thin film portion and the scintillator are curved in a direction opposite to a direction of curvature of the reinforcing member; and
the curved thin film portion and the scintillator and the convexly curved reinforcing member are bonded together.

7. The radiological image detection apparatus according to claim 5, wherein:
the reinforcing member, the thin film portion, and the scintillator are curved in a direction opposite to a direction of curvature of the reinforcing member while the reinforcing member and the thin film portion remain bonded together;
the support is convexly curved toward the radiation entrance side; and
the reinforcing member, the thin film portion, and the scintillator are bonded to the support.

8. The radiological image detection apparatus according to claim 1, wherein:
the reinforcing member is formed from an X-ray absorbent material whose X-ray absorbency is lower than X-ray absorbency of a glass material; and
an aluminum equivalent of the reinforcing member with respect to X radiation emitted at a tube voltage of 60 kV is under 1.8 mm.

9. The radiological image detection apparatus according to claim 8, wherein:
the aluminum equivalent with respect to the X radiation emitted at the tube voltage of 60 kV when the support and the reinforcing member are used is under 1.8 mm.

10. The radiological image detection apparatus according to claim 8, wherein:
the low X-ray absorbent material is metal (including a metal compound and an alloy) and/or a resin.

11. The radiological image detection apparatus according to claim 10, wherein:
the reinforcing member includes a resin layer and a light reflection layer made of metal provided on an X-ray entrance side of the resin layer.

12. The radiological image detection apparatus according to claim 1, wherein:
the reinforcing member is a light reflection member that reflects fluorescence emitted from the scintillator toward the thin film portion.

13. The radiological image detection apparatus according to claim 12, wherein:
the reinforcing member and the thin film portion are bonded together while an adhesive layer is sandwiched therebetween; and
a thickness of the adhesive layer is 100 micrometers or less.

14. The radiological image detection apparatus according to claim 1, wherein:
at least a part of the thin film portion is formed from an amorphous oxide or an organic material.

15. The radiological image detection apparatus according to claim 1, wherein:
the scintillator includes a columnar portion formed from a group of columnar crystals resultant from columnar growth of crystals of a fluorescent material.

16. The radiological image detection apparatus according to claim 1, wherein:
the reinforcing member is provided on a surface of the thin film portion from which a substrate supporting the thin film portion has been peeled off.

17. A radiographic imaging cassette comprising the radiological image detection apparatus according to claim 1, wherein:
the radiological image detection apparatus main body is accommodated in a housing formed by inclusion of the support.

18. A radiographic imaging system comprising:
a radiation source that emits radiation to the subject;
the support; and
the radiological image detection apparatus according to claim 1.

19. A radiological image detection apparatus comprising:
a scintillator that converts radiation emitted by way of a subject into fluorescence and a photodetecting unit provided on a radiation entrance side of the scintillator, wherein:
the photodetecting unit has a thin film portion for detecting the fluorescence as an electric signal and a reinforcing member disposed on another side of the thin film portion with respect to its side facing the scintillator;
the reinforcing member and a support for supporting the subject are bonded together and remain in close contact with each other along a joint plane therebetween;
the reinforcing member and the thin film portion are bonded together; and
bonding strength exerted between the reinforcing member and the thin film portion is greater than bonding strength exerted between the reinforcing member and the support.

* * * * *